(12) United States Patent
Choi

(10) Patent No.: US 9,956,197 B2
(45) Date of Patent: *May 1, 2018

(54) PHENYL CARBAMATE COMPOUNDS FOR USE IN PREVENTING OR TREATING PEDIATRIC EPILEPSY AND EPILEPSY-RELATED SYNDROMES

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/190,123

(22) Filed: Jun. 22, 2016

(65) Prior Publication Data

US 2016/0296493 A1 Oct. 13, 2016

Related U.S. Application Data

(62) Division of application No. 14/204,298, filed on Mar. 11, 2014.

(60) Provisional application No. 61/776,926, filed on Mar. 12, 2013.

(51) Int. Cl.
| | |
|---|---|
| *A61K 31/03* | (2006.01) |
| *A61K 31/27* | (2006.01) |
| *C07C 271/24* | (2006.01) |
| *C07C 271/12* | (2006.01) |
| *A61K 31/325* | (2006.01) |

(52) U.S. Cl.
CPC ............ *A61K 31/325* (2013.01); *A61K 31/03* (2013.01); *A61K 31/27* (2013.01); *C07C 271/12* (2013.01); *C07C 271/24* (2013.01); *C07C 2601/02* (2017.05); *C07C 2601/14* (2017.05); *C07C 2601/16* (2017.05); *C07C 2602/42* (2017.05)

(58) Field of Classification Search
CPC .... A61K 31/03; A61K 31/27; C07C 2601/02; C07C 271/12; C07C 271/24
See application file for complete search history.

(56) References Cited

U.S. PATENT DOCUMENTS

| | | | |
|---|---|---|---|
| 3,265,728 A | 8/1966 | Bossinger et al. | |
| 3,313,692 A | 4/1967 | Bossinger et al. | |
| 3,313,696 A | 4/1967 | Bossinger et al. | |
| 3,313,699 A | 4/1967 | Bossinger et al. | |
| 3,313,700 A | 4/1967 | Bossinger et al. | |
| 3,509,162 A | 4/1970 | Besendorf et al. | |
| 5,258,397 A | 11/1993 | Lepage et al. | |
| 5,698,588 A | 12/1997 | Choi et al. | |
| 5,854,283 A | 12/1998 | Choi et al. | |
| 6,103,759 A | 8/2000 | Choi et al. | |
| 6,127,412 A | 10/2000 | Choi et al. | |
| 6,589,985 B2 | 7/2003 | Plata-Salaman et al. | |
| 7,737,141 B2 | 6/2010 | Kimura et al. | |
| 7,863,499 B2 | 1/2011 | Scantlebury et al. | |
| 2001/0034365 A1 | 10/2001 | Choi et al. | |
| 2002/0156127 A1 | 10/2002 | Plata-Salaman et al. | |
| 2002/0165273 A1 | 11/2002 | Plata-Salaman et al. | |
| 2006/0194873 A1 | 8/2006 | Choi et al. | |
| 2008/0090903 A1 | 4/2008 | Pandey et al. | |
| 2008/0103198 A1 | 5/2008 | Haas | |
| 2008/0260813 A1 | 10/2008 | Thakur et al. | |
| 2008/0317883 A1 | 12/2008 | Choi et al. | |
| 2009/0048213 A1 | 2/2009 | Kimura et al. | |
| 2010/0048629 A1 | 2/2010 | Gage | |
| 2010/0210590 A1 | 8/2010 | Watterson et al. | |
| 2011/0152362 A1 | 6/2011 | Choi et al. | |
| 2012/0184762 A1 | 7/2012 | Choi | |
| 2013/0005801 A1 | 1/2013 | Choi | |
| 2013/0165408 A1 | 6/2013 | Choi | |
| 2013/0165409 A1 | 6/2013 | Choi | |
| 2013/0165410 A1 | 6/2013 | Choi | |
| 2013/0165509 A1 | 6/2013 | Choi | |
| 2013/0184338 A1 | 7/2013 | Choi | |
| 2013/0203846 A1 | 8/2013 | Choi | |
| 2014/0275243 A1 | 9/2014 | Choi | |

FOREIGN PATENT DOCUMENTS

| | | |
|---|---|---|
| CN | 1208402 A | 2/1999 |
| JP | 61-271992 A | 12/1986 |
| JP | 61271992 A | 12/1986 |
| JP | 2002-515029 A | 5/2002 |
| JP | 2008-513466 A | 5/2008 |
| KR | 10-0197901 B1 | 6/1999 |
| KR | 10-2013-0098401 A | 9/2013 |
| WO | WO-02/067923 A1 | 9/2002 |
| WO | WO-02/067925 A1 | 9/2002 |
| WO | WO-2006/033947 A1 | 3/2006 |

(Continued)

OTHER PUBLICATIONS

"U.S. Appl. No. 14/204,298, Non Final Office Action dated Feb. 22, 2016", 23 Pgs.
"U.S. Appl. No. 14/204,298, Preliminary Amendment dated Dec. 1, 2014", 3 pgs.
"U.S. Appl. No. 14/204,298, Response filed Dec. 1, 2015 to Restriction Requirement dated Oct. 1, 2015", 13 pgs.
"U.S. Appl. No. 14/204,298, Restriction Requirement dated Oct. 1, 2015", 9 pgs.
"Epilepsy Definition—Diseases and Conditions—Mayo Clinic", [online]. (c) 1998-2014 Mayo Foundation. [retrieved on Mar. 7, 2014]. Retrieved from the Internet: <URL: http://www.mayoclinic.org/diseases-conditions/epilepsy/basics/definition/con-200337 . . . >, (2014), 13 pgs.
"*Graham v. John Deere Co.*, 383 U.S. 1 (1966)", *Graham et al. v. John Deere Co. of Kansas City et al.* Certiorari to the United States Court of Appeals for the Eighth Circuit. No. 11., (1965-1966), 16 pgs.

(Continued)

*Primary Examiner* — Kendra D Carter
(74) *Attorney, Agent, or Firm* — Schwegman Lundberg & Woessner, P.A.

(57) ABSTRACT

The present invention provides a pharmaceutical composition for preventing and/or treating a pediatric epilepsy or epilepsy-related syndrome comprising the phenyl carbamate compound as an active ingredient, and a use of the phenyl carbamate compound for preventing and/or treating pediatric epilepsy or pediatric epilepsy-related syndromes.

6 Claims, 1 Drawing Sheet

(56) References Cited

FOREIGN PATENT DOCUMENTS

| WO | WO-2006033947 A2 | 3/2006 |
|---|---|---|
| WO | WO-2007/008551 A2 | 1/2007 |
| WO | WO-2008013213 A1 | 1/2008 |
| WO | WO-2008/048802 A1 | 4/2008 |
| WO | WO-2008124848 A1 | 10/2008 |
| WO | WO-2010137351 A1 | 12/2010 |
| WO | WO-2012002773 A2 | 1/2012 |
| WO | WO-2013/100570 A1 | 7/2013 |
| WO | WO-2013/100571 A1 | 7/2013 |

OTHER PUBLICATIONS

"International Application Serial No. PCT/KR2012/011469, International Search Report dated Apr. 22, 2013", 4 pgs.
"International Application Serial No. PCT/KR2012/011469, Written Opinion dated Apr. 22, 2013", 7 pgs.
"International Application Serial No. PCT/KR2012/011470, International Search Report dated Apr. 22, 2013", 4 pgs.
"International Application Serial No. PCT/KR2012/011470, Written Opinion dated Apr. 22, 2013", 5 pgs.
"International Application Serial No. PCT/KR2012/011471, International Search Report dated Apr. 22, 2013", 4 pgs.
"International Application Serial No. PCT/KR2012/011471, Written Opinion dated Apr. 22, 2013", 5 pgs.
"International Application Serial No. PCT/KR2012/011472, International Search Report dated Apr. 22, 2013", 4 pgs.
"International Application Serial No. PCT/KR2012/011472, Written Opinion dated Apr. 22, 2013", 5 pgs.
"International Application Serial No. PCT/KR2012/011474, International Search Report dated Apr. 23, 2013", 4 pgs.
"International Application Serial No. PCT/KR2012/011474, Written Opinion dated Apr. 23, 2013", 6 pgs.
"International Application Serial No. PCT/KR2012/011475, International Search Report dated Apr. 23, 2013", 4 pgs.
"International Application Serial No. PCT/KR2012/011475, Written Opinion dated Apr. 23, 2013", 5 pgs.
"International Serial No. PCT/KR2014,001903, International Search Report dated Jun. 25, 2014", 5 pgs.
"International Serial No. PCT/KR2014/001903, Written Opinion dated Jun. 25, 2014", 6 pgs.
"International Serial No. PCT/KR2014/002005, International Search Report dated Jun. 24, 2014", 5 pgs.
"International Serial No. PCT/KR2014/002005, Written Opinion dated Jun. 24, 2014", 6 pgs.
"International Serial No. PCT/KR2014/002006, International Search Report dated Jun. 27, 2014", 4 pgs.
"International Serial No. PCT/KR2014/002006, Written Opinion dated Jun. 27, 2014", 8 pgs.
"International Serial No. PCT/KR2014/002007, International Search Report dated Jun. 27, 2014", 4 pgs.
"International Serial No. PCT/KR2014/002007, Written Opinion dated Jun. 27, 2014", 6 pgs.
Amarante, Giovanni W, et al., "Acyloins from Morita-Baylis-Hillman adducts: an alternative approach to the racemic total synthesis of bupropion", Tetrahedron Letters 49, (2008), 3744-3748.
Bausch, Cory C., et al., "Cross Silyl Benzoin Additions Catalyzed by Lanthanum Tricyanide", The Journal of Organic Chemistry 69(12), (May 19, 2004), 4283-4285.
Choi, Yong Moon, "Process for Preparation of Phenylpropyl Carbamate Derivatives", Korean Application Serial No. 10-2011-0049932, filed May 26, 2011, (w/ English Translation), 16 pgs.
Choi, Yong Moon, "Process for Preparation of Phenylpropyl Carbamate Derivatives", U.S. Appl. No. 61/432,228, filed Jan. 13, 2011, 12 pgs.
Edin, Michaela, et al., "Ruthenium- and lipase-catalyzed DYKAT of 1,2-diols: an enantioselective synthesis of syn-1,2-diacetates", Tetrahedron: Asymmetry, 17(4), (2006), 708-715.
Girijavallabhan, V. M., et al., "Synthesis of the Antifungal Agent Sch 42427 (SM 9164)", Bioorganic & Medicinal Chemistry Letters, 1(7), (1991), 349-352.
J, G, "Cannon Chapter Nineteen in Burger's Medicinal Chemistry and Drug Discovery", vol. I: Principles and Practice, Wiley-Interscience, (1995), 783-802.
Jiao, P., et al., "A Sequential O-Nitrosoaldol and Grignard Addition Process: An Enantio-and Diastereoselective Entry to Chiral 1,2-Diols", Angewandte Chemie, International Edition, 48(18), (2009), 3333-3336.
Jiao, Peng, et al., "A Sequential O-Nitrosoaldol and Grignard Addition Process: An Enantio- and Diastereoselective Entry to Chiral 1,2-Diols", Angewandte Chemie International Edition 48, (2009), 3333-3336.
Kung, Ching-Hsin, et al., "Carbamate derivatives of felbamate as potential anticonvulsant agents", Medicinal Chemistry Research, 19(5), (2010), 498-513.
Lehmkuhle, M. J, et al., "A Simple Quantitative Method for Analyzing Electrographic Status Epilepticus in Rats", J. Neurophysiol., 101, (2009), 1660-1670.
Ono, T., et al., "Carisbamate acutely suppresses spasms in a rat model of symptomatic infantile spasms", Epilepsia, 52(9), (2011), 1678-1684.
Scantlebury, M. H., et al., "A Model of Symptomatic Infantile Spasms Syndrome", Neurobiol. Dis., 37(3), (2010), 604-612.
Sheridan, R P, "Common Replacements in Drug-Like Compounds", J. Chem. Inf. Comput. Sci, (2002), 103-108.
Suchomelova, L., et al., "Treatment of Experimental Status Epilepticus in Immature Rats: Dissociation Between Anticonvulsant and Antiepileptogenic Effects", Pediatric Research, 59(2), (2006), 237-243.
Toth, Peter P, et al., "Commonly Used Muscle Relaxant Therapies for Acute Low Back Pain: A Review of Carisoprodol, Cyclobenzaprine Hydrochloride, and Metaxalone", Clinical Therapeutics 26(9), (2004), 1355- 1367.
Wijesekera, Lokesh C., et al., "Amyotrophic lateral sclerosis: Review", Orphanet Journal of Rare Diseases, 4(3), (2009), 1-22.
Laxmikant, S., et al., "Carisbamate prevents the development and expression of spontaneous recurrent epileptiform discharged and is neuroprotective in cultured hippocampal neurons", *Epilepsia*, 49(10), (2008), 1795-1802.
Tasker, R. C., et al., "Emergency treatment of acute seizures and status epilepticus", *Archives of Disease in Childhood*, 79(1), (1998), 78-83.

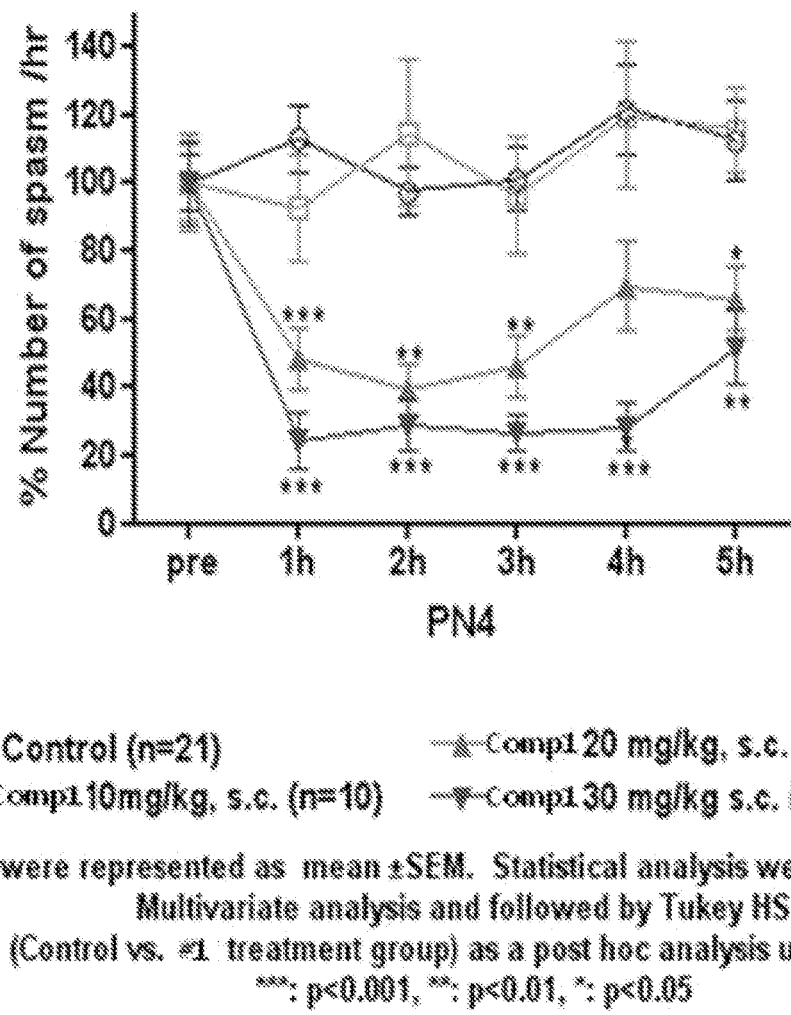

PHENYL CARBAMATE COMPOUNDS FOR USE IN PREVENTING OR TREATING PEDIATRIC EPILEPSY AND EPILEPSY-RELATED SYNDROMES

CROSS-REFERENCE TO RELATED APPLICATIONS

This application is a divisional of and claims the benefit of priority to U.S. application Ser. No. 14/204,298, filed Mar. 11, 2014, which claims the benefit of priority to U.S. Provisional Application No. 61/776,926, filed on Mar. 12, 2013, the entire contents of which are incorporated herein by reference.

The present invention provides a pharmaceutical composition for preventing and/or treating a pediatric epilepsy or epilepsy-related syndrome comprising the phenyl carbamate compound as an active ingredient, and a use of the phenyl carbamate compound for preventing and/or treating pediatric epilepsy or pediatric epilepsy-related syndromes.

BACKGROUND

Epilepsy and its related syndromes may be classified according to whether the associated seizures are partial or generalized, and whether the etiology is idiopathic or symptomatic/cryptogenic. Several important pediatric syndromes can be further grouped according to age of onset and prognosis. Epilepsy is one of the most common and disabling neurologic disorders in childhood. These may be divided into the epileptic encephalopathies of infancy and early childhood, febrile convulsions, and benign partial and generalized syndromes of later childhood and adolescence.

At present, the International League Against Epilepsy classification of epilepsy syndromes according to presumed localization (partial, generalized, undetermined) and etiology (idiopathic, cryptogenic, symptomatic). In clinical practice, it is often useful to conceptualize epilepsy syndromes according to their usual age at presentation, which greatly facilitates syndrome identification in new patients and recognizes the age-related expression of many childhood epilepsies. Definitional problems exist for many pediatric epilepsy syndromes, particularly the epileptic encephalopathies of early infancy, the benign epilepsies of infancy and childhood, the myoclonic epilepsies of infancy and early childhood, and the idiopathic generalized epilepsies of childhood and adolescence. (Epilepsia. 1996; 37 Suppl 1:S26-40).

TABLE 1

Epilepsy syndromes according to usual age at onset

| Period | Epilepsy classification |
| --- | --- |
| Neonatal period | Benign neonatal convulsions |
| | Benign neonatal familial convulsions |
| | Miscellaneous neonatal seizures |
| Infancy | Febrile seizures |
| | Early infantile epileptic encephalopathy |
| | Early myoclonic encephalopathy |
| | Infantile spasm |
| | West syndromes |
| | Severe myoclonic epilepsy of infancy |
| | Benign myoclonic epilepsy of infancy |
| | Benign partial epilepsy of infancy |
| | Benign infantile familial convulsion |
| | Symptomatic/cryptogenic partial epilepsies |

TABLE 1-continued

Epilepsy syndromes according to usual age at onset

| Period | Epilepsy classification |
| --- | --- |
| Early childhood (toddler and preschool age) | Epilepsy with myoclonic absences |
| | Lennox-Gastaut syndrome |
| | Epilepsy with myoclonic-astatic seizures (Doosesyndrome) |
| | Acquired epileptic aphasia (Landaw-Kleffner syndrome) |
| | Epilepsy with continuous spike-wave during low-wave sleep |
| | Epilepsy with gastric seizures and hypothalamic hamartoma |
| | Symptomatic/cryptogenic partial epilepsies |
| Childhood (School age), adolescence and young adulthood | Childhood absence epilepsy |

Some childhood-onset epilepsy syndromes are well defined and easily recognizable. These include benign rolandic, various syndromes with absence, the Landau-Kleffner syndrome (LKS), and continuous spike-wave inslow sleep. Others have somewhat vague characteristics including the Lennox-Gastaut syndrome. Some are still very difficult to define including benign occipital epilepsy and myoclonic-astatic epilepsy.

The term benign epilepsy is used to refer to a group of pediatric epileptic disorders in which remission and lack of significant neurologic sequalae are expected in the vast majority of patients. These disorders are idiopathic, occur in otherwise healthy children, and have (with rare exceptions) a strong genetic component. They include generalized epilepsies and partial epilepsies. These epilepsies are presented according to the age of onset, starting from the neonatal period. Although the prognosis of neonatal convulsions remains poor, benign neonatal convulsions are differentiated by their generally good prognosis. Two syndromes in which no metabolic, hypoxic-ischemic, or structural etiology is apparent are benign familial neonatal convulsions and benign idiopathic neonatal convulsions. (Regarding the former syndrome, some authors prefer to identify it by the term familial neonatal convulsions, dispensing with the adjective benign.) These include generalized, as well as partial, epilepsies. The generalized epilepsies discussed are limited to childhood absence epilepsy, which is also called pyknolepsy, and juvenile absence epilepsy, also known as epilepsy with nonpyknoleptic absences or epilepsy with spanioleptic absences. The benign partial epilepsies include benign partial epilepsy of childhood with centrotemporal spikes, benign occipital epilepsy, and benign epilepsy with affective symptoms.

In addition, presentation of variability of features as well as recent genetic findings and correlations have led to an expansion of the syndrome to include Benign Myoclonic Epilepsy (BME), Severe Myoclonic Epilepsy of Infancy Borderland (SMEB), Severe Infantile Multifocal Epilepsy (SIMFE), and Intractable Childhood Epilepsy with Generalized Tonic Clonic Seizures (ICE-GTC), Dravet syndrome (Ds), also known as Severe Myoclonic Epilepsy of Infancy (SMEI), is a rare and catastrophic form of intractable epilepsy that begins in infancy. Initial seizures are most often prolonged events and in the second year of life other seizure types begin to emerge. Development remains on track initially, with plateaus and a progressive decline typically beginning in the second year of life. Individuals with Dravet syndrome face a higher incidence of SUDEP (sudden unexplained death in epilepsy) and have associated conditions, which also need to be properly treated and managed. SIMFE presents in infancy but the neuro-developmental regression occurs between ages 3 and 6 years instead of between ages 2 and 4 years in the Dravet syndrome.

Lennox-Gastaut Syndrome (LGS) also known as Lennox syndrome, is a difficult-to-treat form of childhood-onset epilepsy that most often appears between the second and sixth year of life, and is characterized by frequent seizures and different seizure types; it is often accompanied by developmental delay and psychological and behavioral problems. As a general rule, the age of seizure onset in LGS patients is between the ages of two and six; however, this does not exclude the possibility that seizures can begin before age two, or after age six. The syndrome shows clear parallels to West syndrome, enough to suggest a connection. West syndrome or West's Syndrome is an uncommon to rare epileptic disorder in infants. Other names for it are Generalized Flexion Epilepsy, Infantile Epileptic Encephalopathy, Infantile Myoclonic Encephalopathy, jackknife convulsions, Massive Myoclonia and Salaam spasms. The term infantile spasms can be used to describe the specific seizure manifestation in the syndrome, but is also used as a synonym for the syndrome itself. West syndrome in modern usage is the triad of infantile spasms, a pathognomonic EEG pattern (called hypsarrhythmia), and developmental regression. Compared with other forms of epilepsy, Pediatric epilepsy is difficult to treat. It is very important that the condition is diagnosed as early as possible and that treatment begins straight away. However, there is no guarantee that therapy will work even in this case. There is to clarify a need for improved medication.

SUMMARY OF THE INVENTION

An embodiment provides a pharmaceutical composition for the prevention and the treatment of a pediatric epilepsy or epilepsy-related symptom, comprising a phenyl carbamate compound of the following Chemical Formula 1, an enantiomer or a diastereomer thereof, or a mixture of enantiomers or diastereomers; or a pharmaceutically acceptable salt thereof.

Another embodiment is to provide a method of preventing and/or treating an epilepsy or an epilepsy-related symptom in pediatric subject comprising administering a pharmaceutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to the pediatric subject in need.

Still other embodiment is to provide a phenyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of epilepsy or the manufacture of a pharmaceutical composition for preventing and/or treating a pediatric epilepsy or an epilepsy-related symptom.

DETAILED DESCRIPTION OF THE EMBODIMENTS

Continuing its research work in the field of epilepsy, the present inventors, as results of studies on the development of the drugs useful for prevention and/or treatment of a pediatric epilepsy or an epilepsy-related symptom, found that a substituted phenyl carbamate compounds of the following Chemical Formula 1 exhibits remarkably excellent anti-epilepsy activity in various emulation models and simultaneously has very low toxicity, and completed the invention.

Therefore, an embodiment provides a pharmaceutical composition for the prevention and the treatment of a pediatric epilepsy or epilepsy-related symptom, comprising an organic compound, i.e., phenyl carbamate derivatives, more particularly, a phenyl carbamate compound represented by following Chemical Formula 1; a racemate, an enantiomer, a diastereomer, a mixture of enantiomers, or a mixture of diastereomers thereof; or a pharmaceutically acceptable salt thereof:

[Chemical Formula 1]

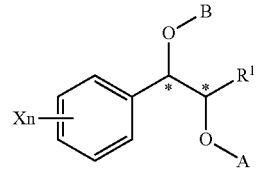

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

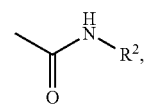

B is hydrogen, a carbamoyl derivative represented by

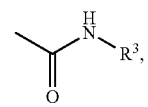

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not carbamoyl derivatives at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

Preferably, in Chemical Formula 1, A is hydrogen and B is carbamoyl group, or A is a carbamoyl group and B is hydrogen.

In the embodiment, in Chemical Formula 1,
if X is F or Br, A and B are not hydrogen at the same time,
if X is chlorine and n is 1 and A and B are hydrogen at the same time, R1 is a C2-C4 linear or branched alkyl group,
if X is chlorine and n is 1, R1 is methyl, isopropyl or butyl, and
if X is bromine located at 4-position of the aromatic ring and n is 1, R1 is methyl, propyl, isopropyl or butyl, and
if A is the carbamoyl represented by, B is hydrogen, R1 is ethyl, and n is 2 at the same time, two X are located at 2 and 3 positions, 2 and 4 positions, 2 and 5 positions, or 3 and 5 positions of the aromatic ring.

In a concrete embodiment, the phenyl carbamate compound may be selected from the group consisting of:
1-(2-chlorophenyl)-1-hydroxypropyl-2-carbamate,
1-(2-chlorophenyl)-1-hydroxybutyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate.

In another concrete embodiment, the compound may not include 1-(2-chlorophenyl)-1,2-propanediol, 1-(2-chlorophenyl)-1-hydroxybutyl-2-carbamate, and 1-(2,6-dichlorophenyl)-1-hydroxybutyl-2-carbamate.

In this compound, 2 chiral carbons exist at positions 1 and 2 from phenyl group substituted with X; thus, the compound may exist in the form of an enantiomer, a diastereomer, a mixture of enantiomers, or a mixture of diastereomers, as well as a racemate.

In an embodiment, the phenyl carbamate compound is selected from the group consisting of:
1-(2-chlorophenyl)-(S)-1-hydroxypropyl-(S)-2-carbamate,
1-(2-chlorophenyl)-(R)-1-hydroxypropyl-(R)-2-carbamate,
racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxybutyl-(S)-2-carbamate,
racemate of 1-(2-chlorophenyl)-(S)-1-hydroxybutyl-(S)-2-carbamate and 1-(2-chlorophenyl)-(R)-1-hydroxybutyl-(R)-2-carbamate,
1-(2-chlorophenyl)-(S)-1-hydroxy-3-methyl-butyl-(S)-2-carbamate,
racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(R)-2-N-isopropylcarbamate,
1-(2-chlorophenyl)-(S)-1-hydroxypropyl-(R)-2-N-cyclopropylcarbamate,
1-(2-chlorophenyl)-(S)-1-hydroxypropyl-(R)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate, 1-(2-iodophenyl)-(R)-1-hydroxypropyl-(R)-2-carbamate, and 1-(2-iodophenyl)-(S)-1-hydroxybutyl-(S)-2-carbamate.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of alkali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

As demonstrated in the following experimental examples, the compound of Chemical Formula 1; a racemate, an enantiomer, a diastereomer, a mixture of enantiomers, or a mixture of diastereomers thereof; or pharmaceutically acceptable salt thereof exhibits an excellent effect on preventing, improving and/or treating epilepsy. Therefore, another embodiment provides a pharmaceutical composition for preventing and/or treating epilepsy containing a phenyl carbamate compound represented by Chemical Formula 1; a racemate, an enantiomer, a diastereomer, a mixture of enantiomers, or a mixture of diastereomers thereof; or a pharmaceutically acceptable salt thereof, as an active ingredient.

Reaction Formula I: Synthesis of Diol-1

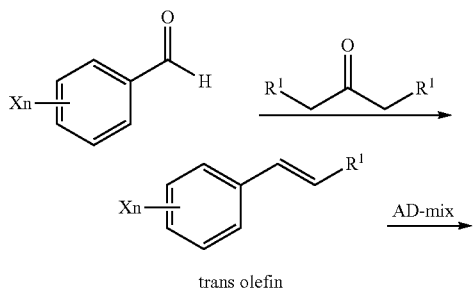

trans olefin

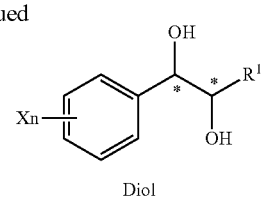

Diol

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

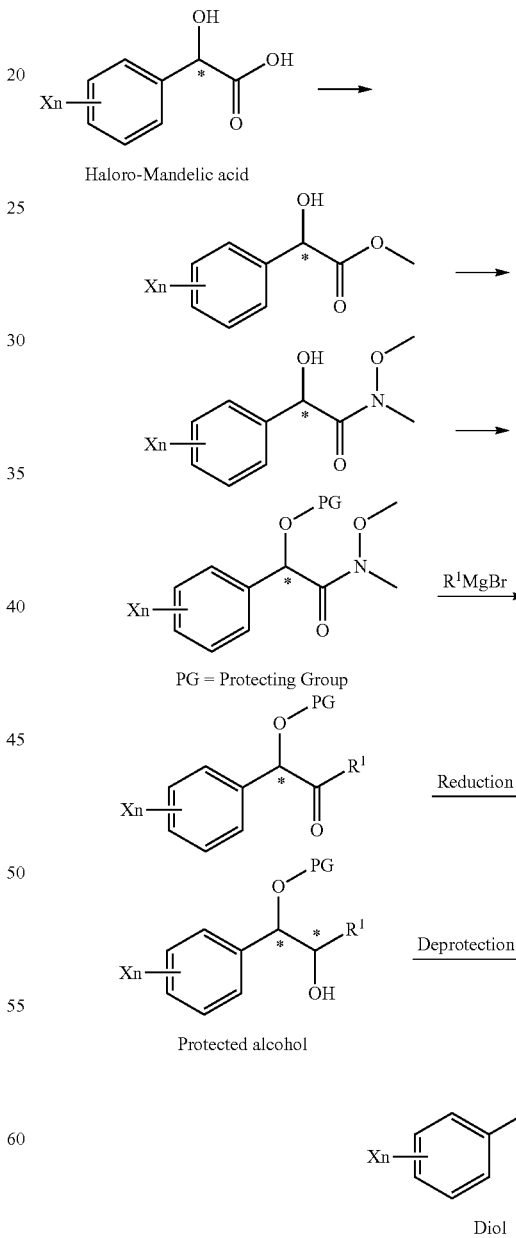

As indicated in the Reaction Formula II, the optically active substance of diol may also be synthesized using an reduction reagent after synthesizing a hydroxy-ketone compound using Haloro-Mandelic acid. In the Reaction Formula II, PG may be Trialkyl Silyl group (TMS, TES, TIPS, TBDMS, TBDPS), Ether group[MOM (Mothoxymethyl ether), MEM (2-Methoxyethoxymethyl ether), BOM (Benzyloxymethyl ether). MTM (Methylthiomethyl ether), SEM (2-(Trimethylsilyl)ethoxymethyl ether), PMBM (p-Methoxybenzyl ether), THP (Tetrahydropyranyl ether), Allyl ether, Trityl ether, Ester group[Ac (acetate), Bz (Benzoate), Pv (Pivaloate), Cbz (Benzyl carbonate), BOC (t-Butyl carbonate), Fmoc (9-Fulorenylmethyl)carbaonate, Alloc (Allyl Carbonate), Troc (Trichloroehtyl carbonate), or p-Methoxybenzoate, Methyl carbonate, and so on.

Reaction Formula I: Synthesis of Diol-1

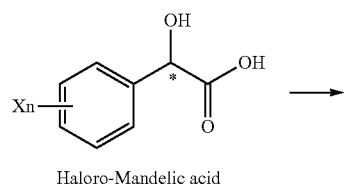

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

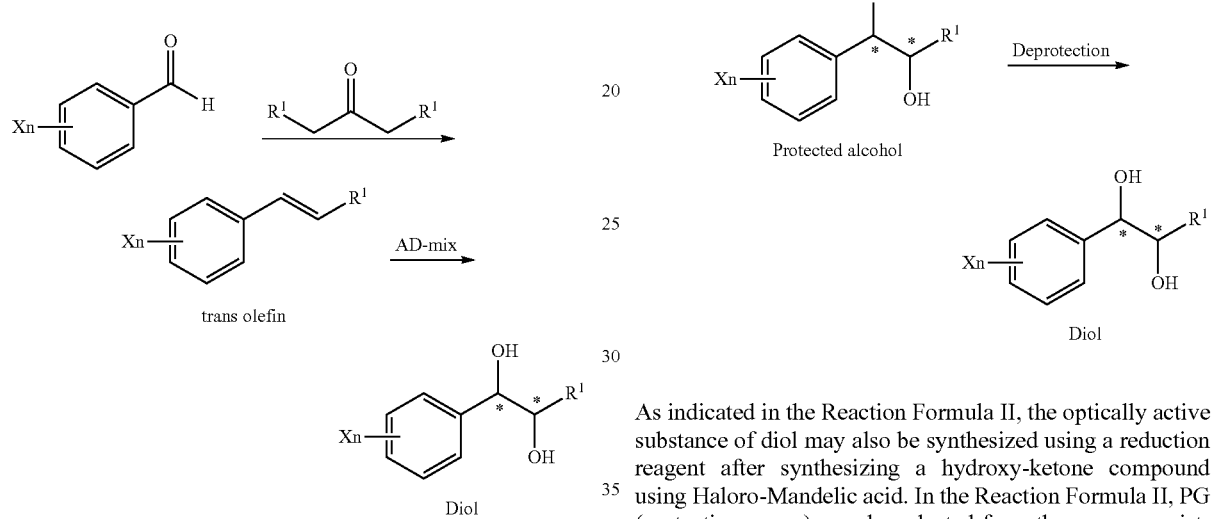

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group[Ac (acetate), Bz (benzoate), Pv(pivaloate), Cbz(benzyl carbonate), BOC(t-butyl carbonate), Fmoc (9-fluorenylmethyl)carbaonate, Alloc(allyl Carbonate), Troc(trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

Reaction Formula III: Carbamation Reaction-1

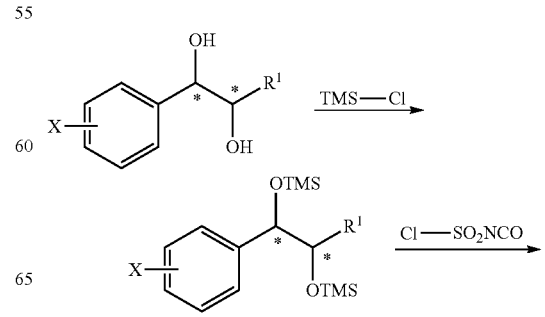

-continued

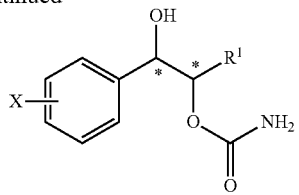

As a highly selectivity form of regioisomer of single carbamate of diol having halogen substituent at phenyl ring. (Example 1~14 and 36~67 are synthesized by reaction formula III.)

Reaction Formula IV: Carbamation Reaction-2

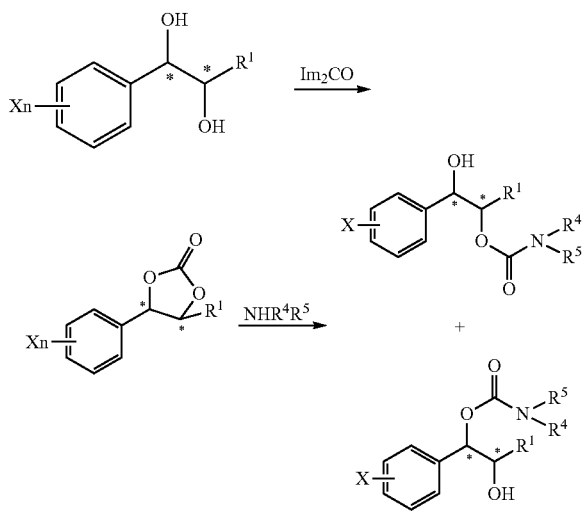

Two substances in the form of regioisomers of a single carbamate of diol having halogen substituent at phenyl ring may be separated by flash column chromatography to obtain two kinds of single carbamate compounds. (Example 15~35 and 68~115 are synthesized by reaction formula IV.)

Reaction Formula V: Protection Reaction

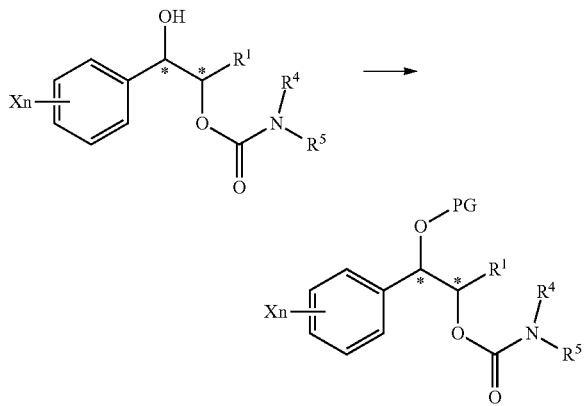

In the Reaction Formula V, PG(protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group[Ac(acetate), Bz(benzoate), Pv(pivaloate), Cbz (benzyl carbonate), BOC(t-butyl carbonate), Fmoc(9-fluorenylmethyl)carbaonate, Alloc(allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

In the Reaction Formula IV and V, R4 and R5 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R4 and R5 may be the same as or different from each other, and independently selected from the group consisting of hydrogen, methyl group, propyl group, isopropyl group, cyclopropyl group, cyclohexyl group, bicycloheptane group, and benzyl group.

Two substances in the form of regioisomers of a single carbamate of diol having halogen substituent at phenyl ring may be separated by flash column chromatography to obtain two kinds of single carbamate compounds.

Another embodiment provides a method of preventing and/or treating a pediatric epilepsy and a pediatric epilepsy-related symptoms comprising administering a pharmaceutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating a pediatric epilepsy and a pediatric epilepsy-related symptoms. The method can be applied for preventing and/or treating an epilepsy and an epilepsy-related symptoms in pediatrics.

The method may further comprise a step of identifying the subject in need of preventing and/or treating a pediatric epilepsy and a pediatric epilepsy-related symptoms prior to the step of administering. Another embodiment provides a phenyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of a pediatric epilepsy and a pediatric epilepsy-related symptoms.

Another embodiment provides a use of a phenyl carbamate compound represented by Chemical Formula 1; a racemate, an enantiomer, a diastereomer, a mixture of enantiomers, or a mixture of diastereomers thereof; or a pharmaceutically acceptable salt thereof for the manufacture of a pharmaceutical composition for preventing and/or treating pediatric epilepsy and pediatric epilepsy-related symptom.

Clinically, an epileptic seizure results from a sudden and abnormal electrical discharge originating from a collection of interconnected neurons in the brain or elsewhere in the nervous system. Depending on the type of epilepsy involved, the resulting nerve cell activity may be manifested by a wide variety of clinical symptoms such as uncontrollable motor movements, changes in the patient's level of consciousness and the like. Epilepsy and epileptic seizures and syndromes may be classified in a variety of ways (See, The Treatment of Epilepsy, Principles & Practice, Third Edition, Elaine Wyllie, M. D. Editor, Lippincott Williams & Wilkins, 2001). However, as used herein the terms; "epilepsy", "epileptic seizures" and "epileptic syndromes" are meant to include all known types of epileptic seizures and syndromes including; partial seizures, including simple, complex and partial seizures evolving to generalized tonic-clonic convulsions and generalized seizures, both convulsive and nonconvulsive and unclassified epileptic seizures.

As used herein, the term "a subject in need of treatment" would include an individual who does not have epilepsy or analogous seizure-related disorder but who may be in a high-risk group for the development of seizures or a seizure related disorder. The terms "subject" or "patient" are used herein interchangeably and as used herein, refer to a human being, who has been the object of treatment, observation or experiment. Herein after, the term "pediatric subject" means human subject in neonatal period, infancy, toddler, Childhood (School age), adolescence and young adulthood. The terms "subject" or "patient" are used herein interchangeably and as used herein, refer to a human being, who has been the object of treatment, observation or experiment.

In an embodiment, the term "pediatric epilepsy-related syndrome" refers to onset of epilepsy syndromes in the periods of neonatal period, infant, the childhood which means usually the birth to age 12, and adolescence. These may be divided into the epileptic encephalopathies of infancy and early childhood, febrile convulsions, and benign partial and generalized syndromes of later childhood and adolescence.

The examples of the pediatric epilepsy and the pediatric epilepsy-related symptoms are listed as Epilepsy syndromes according to usual age at onset in Epilepsia. 1996; 37 Suppl 1:S26-40. Particularly, the examples of the pediatric epilepsy and the pediatric epilepsy-related symptoms include benign myoclonic epilepsy of infancy, benign partial epilepsy of infancy with complex partial seizure, benign partial epilepsy with secondarily generalized seizures in infancy, benign infantile familial convulsions, infantile spasm, Lennox-Gastaut syndrome, Childhood absence epilepsy, West's syndrome, rolandic epilepsy, benign focal epilepsy of childhood, Benign centrotemporal lobe epilepsy of childhood, Benign occipital epilepsy of childhood, Juvenile absence epilepsy, and Juvenile myoclonic epilepsy.

In an embodiment, the pediatric epilepsy or a pediatric epilepsy-related syndrome is selected from the group consisting of Benign Myoclonic Epilepsy(BME), Severe Myoclonic Epilepsy of Infancy Borderland(SMEB), Severe Infantile Multifocal Epilepsy(SIMFE), and Intractable Childhood Epilepsy with Generalized Tonic Clonic Seizures (ICE-GTC), Dravet syndrome(Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes, Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Epilepsy with myoclonic-astatic seizures (Doose syndrome), Acquired epileptic aphasia (Landaw-Kleffner syndrome), Epilepsy with continuous spike-wave during low-wave sleep, Epilepsy with gastric seizures and hypothalamic hamartoma, Symptomatic/cryptogenic partial epilepsies, and Childhood absence epilepsy.

Lithium-pilocarpine induced Status epilepticus (SE) is a frequent neurologic emergency. SE is common in infants and toddlers, with more than 50% of cases of SE occurring under the age of 2 years. SE is associated with an increased risk of developing epilepsy. 30% of children presenting with SE were found to develop epilepsy subsequently. More recently, 41% of patients with acute symptomatic SE (one-third were children) developed epilepsy within the next 10 y (Treatment of Experimental Status Epilepticus in Immature Rats: Dissociation Between Anticonvulsant and Anti-epileptogenic Effects (2006), PEDIATRIC RESEARCH, SUCHOMELOVA et. al.).

Picrotoxin is thought to induce generalised convulsive seizure (Picrotoxin-induced generalized convulsive seizure in rat: changes in regional distribution and frequency of the power of electroencephalogram rhythms (2002), Clin Neurophysiol. April; 113(4):586-96. Mackenzie L et al.)

PTZ test is thought to be predictive of anticonvulsant drug activity against nonconvulsive (absence or myoclonic) seizures (Critical review of current animal models of seizures and epilepsy used in the discovery and development of new antiepileptic drugs(2011), Seizure 20, 359-368, Wolfgang Loscher). 6Hz test is Minimal Clonic Seizure. Multiple-hit rat model of IS is thought to be predictive of ACTH (Adrenocorticotropic hormone)-refractory infantile spasm, may be Lennox-Gastaut syndrome and West syndrome because Children with infantile spasms present typically between 4 and 18 months of age(U.S. Pat. No. 7,863,499).

Lennox-Gastaut syndrome has an onset between 3 and 5 years of age and is characterized by intractable mixed seizures with a combination of tonic, myoclonic, atonic, and absence seizures. Children between 3 and 13 years of age who suffer from benign rolandic epilepsy experience nighttime seizures during sleep. Juvenile myoclonic epilepsy of Janz is inherited as an autosomal dominant trait that manifests in early adolescence (onset 12-18 years of age). Patients experience myoclonic jerks typically on awakening but may also have tonic-clonic (80%) or absence (25%) seizures. Children with infantile spasms or West's syndrome present typically between 4 and 18 months of age.

West syndrome is an epileptic syndrome characterized by the triad of infantile spasm (generalized seizures), hypsarrhythmia (chaotic, abnormal EEG pattern), and arrest of psychomotor development at seizure onset (Wong & Trevathan, 2001). It occurs in approximately 0.7/100,000 people and accounts for 28-30% of infants with epilepsy. The age of onset is usually around 3 to 12 months with peak at 4-7 months (Dulac, 2001). Males tend to be at a greater risk of acquiring West syndrome than females. A family history of infantile spasms is reported in 3-6% of cases. Prenatal causes of West syndrome include tuberous sclerosis, intrauterine infections, brain malformations, and inborn errors of metabolism. Postnatal causes include cerebral hypoxic events, head trauma, and infections. Cognitive impairment is found in approximately 60-70% of patients at onset of infantile spasms. The seizure characteristics found in West syndrome include a sudden onset of a tonic seizure that is bilateral and symmetrical. The spasms may vary from massive contractions of large muscle groups to contractions of only neck and abdominal muscles. A patient may have more than one type of spasm and they tend to occur in clusters of 5-10 individual spasms. An aura or warning signal such as a cry may precede the seizure. Approximately 30% of symptomatic West syndrome patients progress to Lennox Gastaut syndrome. Treatment for West syndrome includes hormonal therapy with adrenocorticotropic hormone (ACTH) or prednisone (Snead, 1996).

Infantile spasm syndrome, or infantile spasms (IS), represents an age-related epileptic syndrome characterized by brief spasms, specific EEG patterns [hysarrhythmia (interictally) and electrodecremental response (ictally)], with frequent subsequent cognitive deterioration. The incidence of IS is 2.5 per 10,000 live births (Bobo et al., 1994; Hrachovy and Frost, 2003) with a slight (60%) male predominance (Webb et al., 1996). The causes of IS are diverse and can be multifacitorial, often a combination of genetic predisposition (Mizukawa et al., 1992; Bingham et al., 1996; Dulac et al., 1993a) and environmental insults (Watanabe, 1998). IS can be classified into symptomatic, cryptogenic and idiopathic groups.

The ILAE classification, 8 typical form of DS(Dravet syndrome), is defined by a refractory and mixed seizure disorder (most commonly myoclonus, atypical absence, and partial seizures) which starts after different types of febrile and afebrile seizures in an, otherwise, healthy infant. In the second year of life, the child develops cognitive and behavioral difficulties (Dravet syndrome, what is new? (2013), Neurosciences, Raidah S. Al-Baradie)

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like. In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like. Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the pharmaceutically effective amount of 0.01 to 750 mg/kg(body weight), preferably 0.1 to 500 mg/kg(body weight) per one day, based on the active ingredient. The pharmaceutically effective amount may refers to an amount capable of exhibiting a desired effect, i,e., an effect of treating and/or preventing epilepsy. The pharmaceutically effective amount may be administered through oral or parenteral pathway (e.g., an intravenous injection, an intramusclular injection, etc.), one or two or more times per one day.

The pharmaceutically effective amount and the administration pathway of the present pharmaceutical composition may be properly adjusted by a person skilled in the relevant field considering the conditions of the subject (patient), desired effects, and the like. The subject may be a mammal including human or cells and/or tissues obtained therefrom.

BRIEF DESCRIPTION OF DRAWINGS

FIG. 1 is a graph showing the test result of Compound 1(1-(2-chlorophenyl)-(S)-1-hydroxypropyl-(S)-2-carbamate) by using Multiple-hit rat model of IS.

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

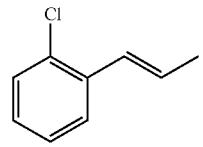

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1$H NMR(400 MHz, $CDCl_3$) δ1.94(d, J=4.8 Hz, 3H), 6.24(m, 1H), 6.78(d, J=14 Hz, 1H),7.11~7.51(m, 4H)

Preparation Example 2

Synthesis of 1-(2-chlorophenyl)-trans-1-butene

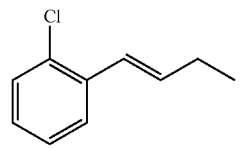

The substantially same method as described in Preparation Example 1 was conducted, except that 3-heptanone was used instead of 3-pentanone, to obtain the title compound (2.9 g, yield 83%).
$^1$H NMR(400 MHz, $CDCl_3$) δ1.14(d, J=7.6 Hz, 3H), 2.29~2.33(m, 2H), 6.28(dt, J=16 Hz, 6.4 Hz, 1H), 6.78(d, J=15.6 Hz, 1H), 7.13~7.54(m, 4H)

Preparation Example 3

Synthesis of 1-(2-chlorophenyl)-3-methyl-trans-1-butene

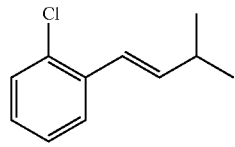

The substantially same method as described in Preparation Example 1 was conducted, except that 2,6-dimethyl-heptan-4-one was used instead of 3-pentanone, to obtain the title compound (8.0 g, yield 50~90%).

$^1$H NMR(400 MHz, CDCl$_3$) δ1.14(d, J=6.8 Hz, 6H), 2.25~2.57(m, 1H), 6.20(dd, J=16 Hz, 7.2 Hz, 1H), 7.64(d, J=16 Hz, 1H), 7.12~7.54(m, 4H)

Preparation Example 4

Synthesis of 1-(2-chlorophenyl)-trans-1-hexene

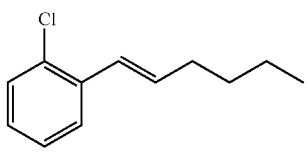

The substantially same method as described in Preparation Example 1 was conducted, except that 6-undecanone was used instead of 3-pentanone, to obtain the title compound (10 g, yield 85%).

$^1$H NMR(400 MHz, CDCl$_3$) δ0.96(t, J=7.2 Hz, 3H), 1.33~1.56(m, 4H), 2.26~2.32(m, 4H), 6.24(dt, J=15.6 Hz, 7 Hz, 1H), 6.78(d, J=16 Hz, 1H), 7.13~7.54(m, 4H)

Preparation Example 5

Synthesis of 1-(2,4-dichlorophenyl)-trans-1-propene

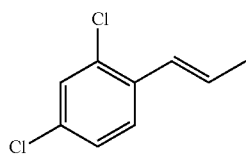

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR(400 MHz, CDCl$_3$) δ1.95(dd, J=6.8 Hz, 1.6 Hz, 3H), 6.24(m, 1H), 6.72(d, J=15.6 Hz, 1H), 7.18~7.44(m, 3H)

Preparation Example 6

Synthesis of 1-(2,4-dichlorophenyl)-trans-1-butene

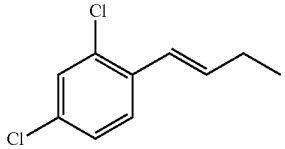

The substantially same method as described in Preparation Example 5 was conducted, except that 3-heptanone was used instead of 3-pentanone, to obtain the title compound (2.1 g, yield 90%).

$^1$H NMR(400 MHz, CDCl$_3$) δ1.14(d, J=7.6 Hz, 3H), 2.20~2.33(m, 2H), 6.26(dt, J=16 Hz, 6.8 Hz, 1H), 6.70(d, J=15.6 Hz, 1H), 7.18~7.46(m, 3H)

Preparation Example 7

Synthesis of 1-(2,6-dichlorophenyl)-3-methyl-trans-1-butene

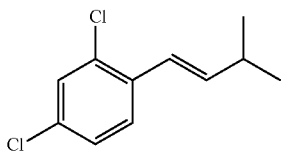

The substantially same method as described in Preparation Example 5 was conducted, except that 2,6-dimethyl-heptan-4-one was used instead of 3-pentanone, to obtain the title compound (0.23 g, yield 10~40%).

$^1$H NMR(400 MHz, CDCl$_3$) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.18~7.46(m, 3H)

Preparation Example 8

Synthesis of 1-(2,4-dichlorophenyl)-trans-1-hexene

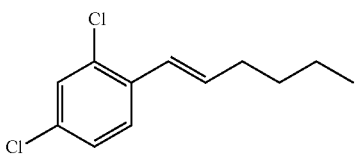

The substantially same method as described in Preparation Example 5 was conducted, except that 6-undecanone was used instead of 3-pentanone, to obtain the title compound (3.2 g, yield 40~80%).

$^1$H NMR(400 MHz, CDCl$_3$) δ0.96(t, J=7.2 Hz, 3H), 1.38~1.52(m, 4H), 2.25~2.31(m, 2H), 6.22(dt, J=15.6 Hz, 6.8 Hz, 1H), 6.70(d, J=15.6 Hz, 1H), 7.18~7.46(m, 3H)

Preparation Example 9

Synthesis of 1-(2,6-dichlorophenyl)-trans-1-propene

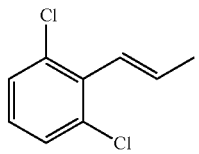

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR(400 MHz, CDCl$_3$) δ1.98(d, J=8 Hz, 3H), 6.23~6.31(m, 1H), 6.40(d, J=16 Hz, 1H),7.05~7.32(m, 3H)

Preparation Example 10

Synthesis of 1-(2,6-dichlorophenyl)-trans-1-butene

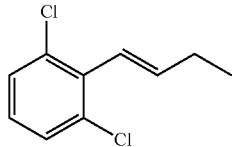

The substantially same method as described in Preparation Example 9 was conducted, except that 3-heptanone was used instead of 3-pentanone, to obtain the title compound (1.2 g, yield 10~40%).

$^1$H NMR(400 MHz, CDCl$_3$) δ1.17(t, J=7.6 Hz, 3H), 2.30~2.37(m, 2H), 6.29(dt, J=16.4 Hz, 6 Hz, 1H), 6.37(d, J=16.4 Hz, 1H),7.05~7.32(m, 3H)

Preparation Example 11

Synthesis of 1-(2,6-dichlorophenyl)-3-methyl-trans-1-butene

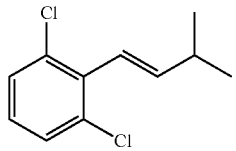

The substantially same method as described in Preparation Example 9 was conducted, except that 2,6-dimethylheptan-4-one was used instead of 3-pentanone, to obtain the title compound (0.23 g, yield 10~40%).

$^1$H NMR(400 MHz, CDCl$_3$) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.05~7.32(m, 3H)

Preparation Example 12

Synthesis of 1-(2,6-dichlorophenyl)-trans-1-hexene

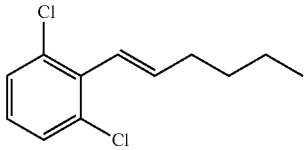

The substantially same method as described in Preparation Example 9 was conducted, except that 6-undecanone was used instead of 3-pentanone, to obtain the title compound (0.2 g, yield 10~40%).

$^1$H NMR(400 MHz, CDCl$_3$) δ0.99(t, J=7.2 Hz, 3H), 1.14~1.59(m, 4H), 2.30~2.36(m, 2H), 6.24(dt, J=16 Hz, 6.6 Hz, 1H),6.38(d, J=16.4 Hz, 1H), 7.05~7.33(m, 3H)

Preparation Example 13

Synthesis of 1-(2,3-dichlorophenyl)-trans-1-propene

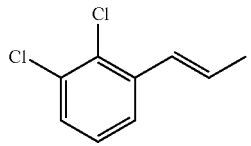

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR(400 MHz, CDCl$_3$) δ1.94(d, J=4.8 Hz, 3H), 6.24(m, 1H), 6.78(d, J=14 Hz, 1H),7.11~7.51(m, 3H)

Preparation Example 14

Synthesis of 1-(2-chlorophenyl)-(S,S)-1,2-propanediol

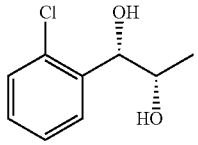

1-(2-chlorophenyl)-trans-1-propene (1.5 g, Preparation Example 1) was dissolved in 30 mL of the mixture of t-BuOH/H$_2$O (1:1(V/V)). At 0° C., AD-mix-α (Aldrich, U.S.A.) (13.7 g) and methane sulfone amide (CH$_3$SO$_2$NH$_2$, 0.76 g, 0.0080 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concented under reduced pressure. The concentrated residue was purified by a silica gel column chromatography to produce the title compound (1.65 g, yield 90%).

¹H NMR(400 MHz, CDCl₃) δ1.20(d, J=6.4 Hz, 3H), 2.48(d, J=4.0 Hz 1H), 2.92(d, J=4.4 Hz, 1H),3.93~3.97(m, 1H), 4.97(t, J=4.8 Hz, 1H),7.22~7.51(m, 4H)
¹³CNMR(100 MHz, CDCl₃) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

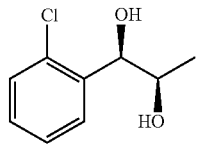

1-(2-chlorophenyl)-trans-1-propene (2.5 g, Preparation Example 1) was dissolved in 50 mL of the mixture of t-BuOH/H₂O (1:1(V/V)). At 0° C., AD-mix-α (Aldrich, U.S.A.) (23.5 g) and methane sulfone amide (CH₃SO₂NH₂, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (2.96 g, yield 90%).
¹H NMR(400 MHz, CDCl₃) δ1.20(d, J=6.4 Hz, 3H), 2.48(d, J=4.0 Hz, 1H), 2.92(d, J=4.4 Hz, 1H),3.93~3.97(m, 1H), 4.97(t, J=4.8 Hz, 1H),7.22~7.51(m, 4H)

Preparation Example 16

Synthesis of the mixture of 1-(2-chlorophenyl)-(S, S)-1,2-propanediol and 1-(2-chlorophenyl)-(R,R)-1, 2-propanediol

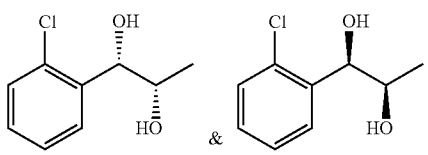

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concented under reduced pressure. The concentrated residue was purified by a silica gel column chromatography to produce the title compound (6.42 g, yield 80%).
¹H NMR(400 MHz, CDCl₃) δ61.20(d, J=6.4 Hz, 3H), 2.48(d, J=4.0 Hz, 1H), 2.92(d, J=4.4 Hz, 1H),3.93~3.97(m, 1H), 4.97(t, J=4.8 Hz, 1H),7.22~7.51(m, 4H)

Preparation Example 17

Synthesis of 1-(2-chlorophenyl)-(S,S)-1,2-butanediol

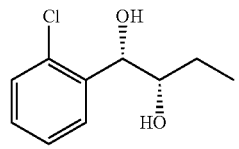

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).
¹H NMR(400 MHz, CDCl₃) δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 18

Synthesis of 1-(2-chlorophenyl)-(R,R)-1,2-butanediol

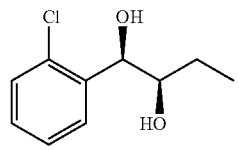

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).
¹H NMR(400 MHz, CDCl₃) δ1.01(t, J=7.4 Hz, 3H), 1.52~1.65(m, 2H), 2.01(d, J=4.4 Hz, 1H), 2.74(d, J=5.2 Hz, 1H),3.69~3.75(m, 1H), 5.05(t, J=5.0 Hz, 1H),7.23~7.54(m, 4H)

Preparation Example 19

Synthesis of the mixture of 1-(2-chlorophenyl)-(S, S)-1,2-butanediol and 1-(2-chlorophenyl)-(R,R)-1,2-butanediol

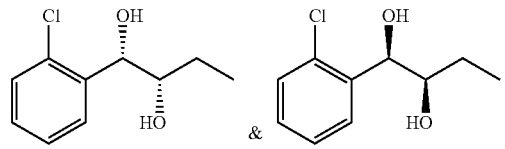

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR(400 MHz, CDCl$_3$) δ1.01(t, J=7.4 Hz, 3H), 1.52~1.65(m, 2H), 2.01(d, J=4.4 Hz, 1H), 2.74(d, J=5.2 Hz, 1H),3.69~3.75(m, 1H), 5.05(t, J=5.0 Hz, 1H),7.23~7.54(m, 4H)

Preparation Example 20

Synthesis of 1-(2-chlorophenyl)-3-methyl-(S,S)-1,2-butanediol

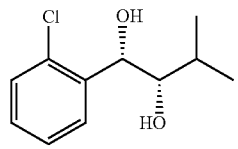

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR(400 MHz, CDCl$_3$) δ1.07(t, J=7.2 Hz, 6H), 1.83~1.89(m, 1H), 1.92(d, J=5.6 Hz, 1H), 2.69(d, J=6.4 Hz, 1H),3.53~3.56(m, 1H),5.22~5.25(m, 1H), 7.23~7.55(m, 4H)

Preparation Example 21

Synthesis of 1-(2-chlorophenyl)-3-methyl-(R,R)-1,2-butanediol

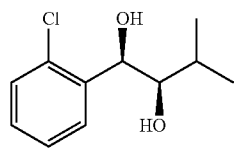

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR(400 MHz, CDCl$_3$) δ1.07(t, J=7.2 Hz, 6H), 1.82~1.90(m, 1H), 1.93(d, J=5.6 Hz, 1H), 2.79(d, J=6 Hz, 1H),3.53~3.57(m, 1H),5.23~5.25(m, 1H), 7.23~7.54(m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

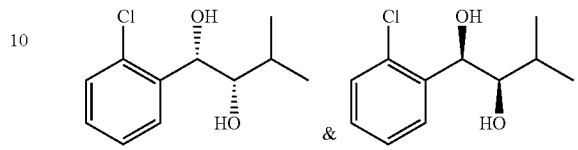

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

$^1$H NMR(400 MHz, CDCl$_3$) δ1.07(t, J=7.2 Hz, 6H), 1.83~1.90(m, 1H), 1.92(d, J=5.6 Hz, 1H), 2.69(d, J=6.4 Hz, 1H),3.53~3.56(m, 1H),5.22~5.25(m, 1H), 7.23~7.55(m, 4H)

Preparation Example 23

Synthesis of 1-(2-chlorophenyl)-(S,S)-1,2-hexanediol

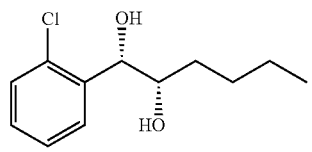

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

$^1$H NMR(400 MHz, CDCl$_3$) δ0.90(t, J=7.2 Hz, 3H), 1.35~1.65(m, 6H), 2.08(d, J=4.4 Hz, 1H), 2.71(d, J=5.2 Hz, 1H),3.78~3.83(m, 1H), 5.04(t, J=5.0 Hz, 1H),7.23~7.53(m, 4H)

Preparation Example 24

Synthesis of 1-(2-chlorophenyl)-(R,R)-1,2-hexanediol

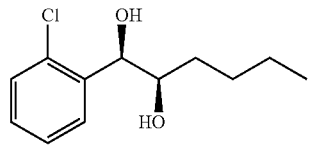

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).

¹H NMR(400 MHz, CDCl₃) δ0.91(t, J=6.6 Hz, 3H), 1.35~1.65(m, 6H), 2.08(d, J=4.8 Hz, 1H), 2.70(d, J=5.2 Hz, 1H),3.80~3.83(m, 1H), 5.05(t, J=5.0 Hz, 1H),7.24~7.56(m, 4H)

Preparation Example 25

Synthesis of the mixture of 1-(2-chlorophenyl)-(S,S)-1,2-hexanediol and 1-(2-chlorophenyl)-(R,R)-1,2-hexanediol

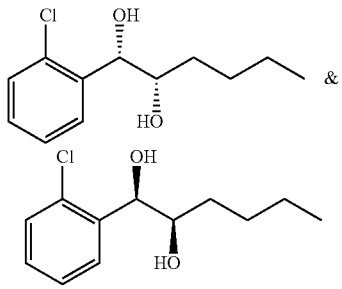

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

¹H NMR(400 MHz, CDCl₃) δ0.90(t, J=7.2 Hz, 3H), 1.26~1.55(m, 6H), 2.08(d, J=4.4 Hz, 1H), 2.71(d, J=5.6 Hz, 1H),3.78~3.84(m, 1H), 5.04(t, J=3.2 Hz, 1H),7.24~7.55(m, 4H)

Preparation Example 26

Synthesis of 1-(2,4-dichlorophenyl)-(S,S)-1,2-propanediol

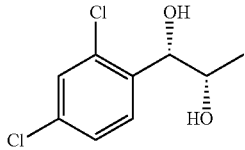

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

¹H NMR(400 MHz, CDCl₃) δ1.22(d, J=6.4 Hz, 3H), 2.10(d, J=4.4 Hz, 1H), 2.71(d, J=4.8 Hz, 1H),3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 27

Synthesis of 1-(2,4-dichlorophenyl)-(R,R)-1,2-propanediol

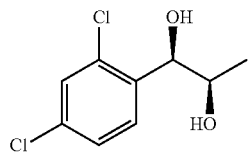

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

¹H NMR(400 MHz, CDCl₃) δ1.22(d, J=6.4 Hz, 3H), 2.10(d, J=4.4 Hz, 1H), 2.71(d, J=4.8 Hz, 1H),3.90~3.95(m, 1H), 4.94(t, J=5.0 Hz, 1H),7.31~7.49(m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

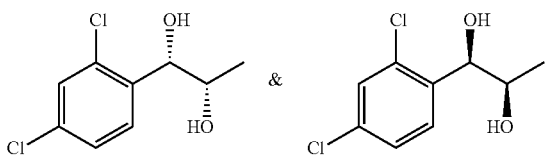

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

¹H NMR(400 MHz, CDCl₃) δ1.22(d, J=6.4 Hz, 3H), 2.10(d, J=4.4 Hz, 1H), 2.71(d, J=4.8 Hz, 1H),3.90~3.95(m, 1H), 4.94(t, J=5.0 Hz, 1H),7.31~7.49(m, 3H)

Preparation Example 29

Synthesis of 1-(2,4-dichlorophenyl)-(S,S)-1,2-butanediol

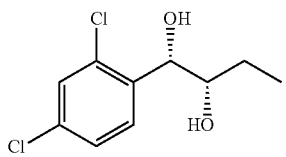

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H),3.65~3.68(m, 1H), 5.01(t, J=5.0 Hz, 1H),7.31~7.49(m, 3H)

Preparation Example 30

Synthesis of 1-(2,4-dichlorophenyl)-(R,R)-1,2-butanediol

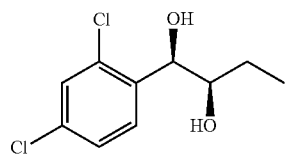

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H),3.65~3.68(m, 1H), 5.01(t, J=5.0 Hz, 1H),7.31~7.49(m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

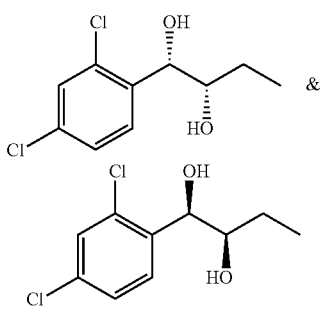

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^1$H NMR(400 MHz, CDCl$_3$) δ1.02(t, J=7.4 Hz, 3H), 1.54~1.61(m, 2H), 2.07(d, J=4.8 Hz, 1H), 2.74(d, J=4.8 Hz, 1H),3.65~3.68(m, 1H), 5.01(t, J=5.0 Hz, 1H), 77.31-7.49(m, 3H)

Preparation Example 32

Synthesis of 1-(2,4-dichlorophenyl)-3-methyl-(S,S)-1,2-butanediol

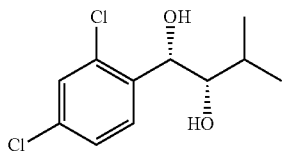

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 33

Synthesis of 1-(2,4-dichlorophenyl)-3-methyl-(R,R)-1,2-butanediol

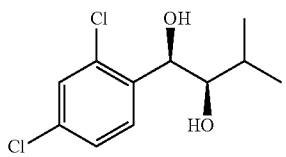

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

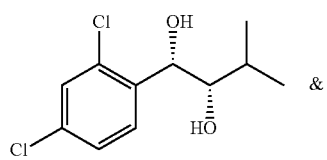

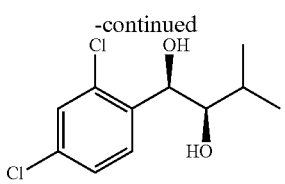

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 35

Synthesis of 1-(2,4-dichlorophenyl)-(S,S)-1,2-hexanediol

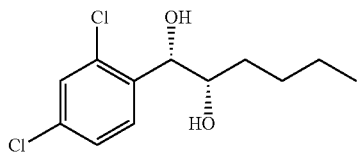

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

$^1$H NMR(400 MHz, CDCl$_3$) δ0.89~0.93(m, 3H), 1.30~1.39(m, 2H), 1.49~1.52(m, 2H),1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H),7.28~7.50(m, 3H)

Preparation Example 36

Synthesis of 1-(2,4-dichlorophenyl)-(R,R)-1,2-hexanediol

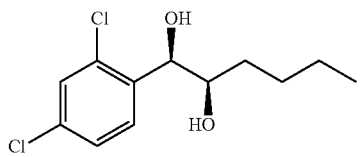 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

$^1$H NMR(400 MHz, CDCl$_3$) δ0.89~0.93(m, 3H), 1.30~1.39(m, 2H), 1.49~1.52(m, 2H),1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H),7.28~7.50(m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

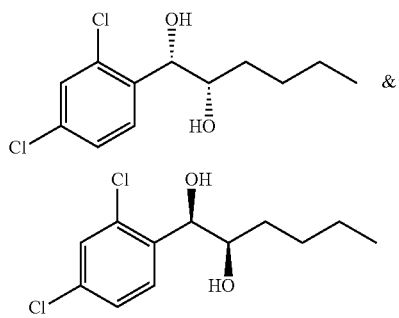

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).

$^1$H NMR(400 MHz, CDCl$_3$) δ0.89~0.93(m, 3H), 1.30~1.39(m, 2H), 1.49~1.52(m, 2H),1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H),7.28~7.50(m, 3H)

Preparation Example 38

Synthesis of 1-(2,6-dichlorophenyl)-(S,S)-1,2-propanediol

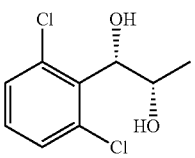

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H),7.18~7.36(m, 3H)

Preparation Example 39

Synthesis of
1-(2,6-dichlorophenyl)-(R,R)-1,2-propanediol

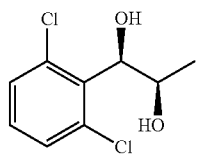

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H),7.18~7.36(m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

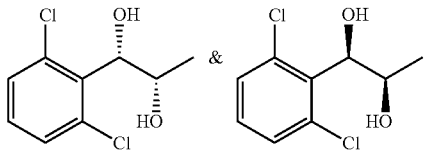

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H),7.18~7.36(m, 3H)

Preparation Example 41

Synthesis of
1-(2,6-dichlorophenyl)-(S,S)-1,2-butanediol

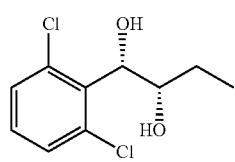

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H),4.22~4.26(m, 1H), 5.26(t, J=8.4 Hz, 1H),7.17~7.35(m, 3H)

Preparation Example 42

Synthesis of
1-(2,6-dichlorophenyl)-(R,R)-1,2-butanediol

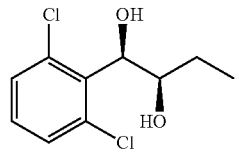

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H),4.22~4.26(m, 1H), 5.26(t, J=8.4 Hz, 1H),7.17~7.35(m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

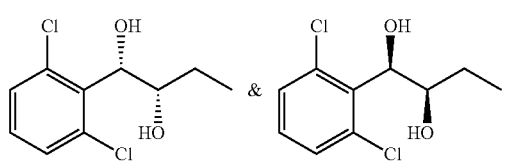

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H),4.22~4.26(m, 1H), 5.26(t, J=8.4 Hz, 1H),7.17~7.35(m, 3H)

Preparation Example 44

Synthesis of 1-(2,6-dichlorophenyl)-3-methyl-(S,S)-1,2-butanediol

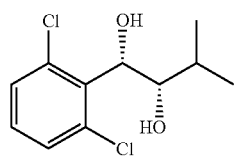

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 45

Synthesis of 1-(2,6-dichlorophenyl)-3-methyl-(R,R)-1,2-butanediol

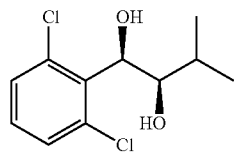

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

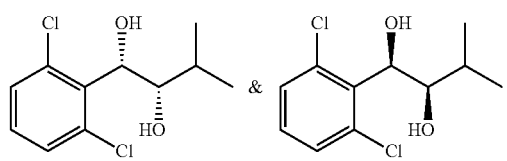

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H),4.13~4.18(m, 1H), 5.36(t, J=7.6 Hz, 1H),7.17~7.35(m, 3H)

Preparation Example 47

Synthesis of 1-(2,6-dichlorophenyl)-(S,S)-1,2-hexanediol

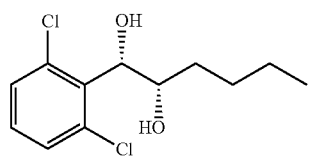 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR(400 MHz, CDCl$_3$) δ0.85(t, J=6.8 Hz, 3H), 1.20~1.31(m, 4H), 1.45~1.53(m, 2H),2.61~2.62(m, 1H), 3.12(d, J=8.4Hz, 1H),4.28~4.33(m, 1H), 5.25(t, J=8.4 Hz, 1H),7.18~7.35(m, 3H)

Preparation Example 48

Synthesis of 1-(2,6-dichlorophenyl)-(R,R)-1,2-hexanediol

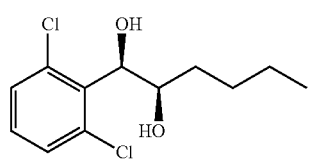 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR(400 MHz, CDCl$_3$) δ0.85(t, J=6.8 Hz, 3H), 1.20~1.31(m, 4H), 1.45~1.53(m, 2H),2.61~2.62(m, 1H), 3.12(d, J=8.4Hz, 1H),4.28~4.33(m, 1H), 5.25(t, J=8.4 Hz, 1H),7.18~7.35(m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

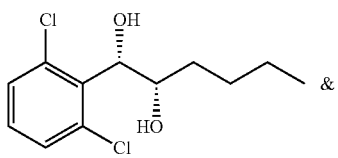

&

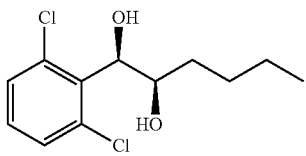

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR(400 MHz, CDCl$_3$) δ0.85(t, J=6.8 Hz, 3H), 1.20~1.31(m, 4H), 1.45~1.53(m, 2H),2.61~2.62(m, 1H), 3.12(d, J=8.4Hz, 1H),4.28~4.33(m, 1H), 5.25(t, J=8.4 Hz, 1H),7.18~7.35(m, 3H)

Preparation Example 50

Synthesis of methyl 2-(2-chlorophenyl)-(R)-2-hydroxyacetate

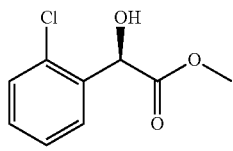

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR(400 MHz, CDCl$_3$) δ3.59(d, J=5.2, 1H), 3.79(t, J=6.0, 3H), 5.59(d, J=5.2, 1H),7.28~7.43(m, 4H)

Preparation Example 51

Synthesis of 2-(2-chlorophenyl)-(R)-2-hydroxy-N-methoxy-N-methylacetamide

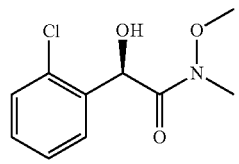

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concented under reduced pressure. The concentrated residue was purified by a silica gel column chromatography to produce the title compound (14.68 g, yield 82%).

$^1$H NMR(400 MHz, CDCl$_3$) δ3.23(s, 3H), 3.28(s, 3H), 4.33(d, J=6.0 Hz, 1H), 5.81(d, J=5.6 Hz, 1H),7.23~7.42(m, 4H)

Preparation Example 52

Synthesis of 2-(2-chlorophenyl)-N-methoxy-(R)-2-(t-butyl dimethlysiloxy)-N-methylacetamide

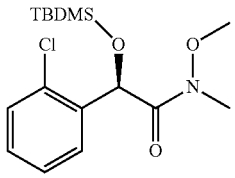

2-(2-chlorophenyl)-(R)-2-hydroxy-N-methoxy-N-methylacetamide (0.81 g, 3.52 mmol) obtained in Preparation Example 51 was dissolved in dichloromethane (DCM), and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with H$_2$O. The organic layer was separated and collected. The aqueous layer was extracted with CH$_2$Cl$_2$ (300 mL), dried over MgSO$_4$. Concentration under vacuum provided a title compound. (0.97 g, 80~95%).

$^1$H NMR(400 MHz, CDCl$_3$) δ−0.03(s, 3H), 0.14(s, 3H), 0.94(s, 9H), 2.97(s, 3H), 3.02(s, 3H), 5.83(s, 1H),7.25~7.60 (m, 4H)

Preparation Example 53

Synthesis of 1-(2-chlorophenyl)-(R)-1-(t-butyldimethyl-siloxy)propane-2-on

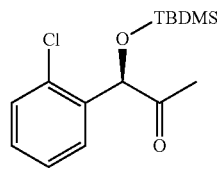

2-(2-chlorophenyl)-N-methoxy-(R)-2-(t-butyldimethylsiloxy)-N-methylacetamide (0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate ($KHSO_4$, 100 ml) and then, washed again with brine. The obtained organic layer was dehydrated with anhydrous magnesium sulfate ($MgSO_4$), filtrated, and concentrated under reduced pressure. The concentrated residue was purified by a silica gel column chromatography to produce the title compound (0.69 g, yield 85-95%).

$^1$H NMR(400 MHz, $CDCl_3$) δ−0.3(s, 3H), 0.14(s, 3H), 0.94(s, 9H), 2.18(s, 3H), 5.50(s, 1H), 7.27~7.56(m, 4H)

Preparation Example 54

Synthesis of 1-(2-chlorophenyl)-(R)-1-(t-butyldimethyl-siloxy)-(S)-2-propanol

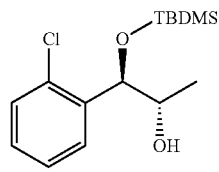

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride ($Zn(BH_4)_2$) was slowly added thereto and the obtained product was stirred. When the reaction was completed, the obtained product was washed by $H_2O$. The obtained organic layer was washed with $H_2O$, dehydrated with anhydrous magnesium sulfate ($MgSO_4$), filtrated, and concentrated under reduced pressure. The concentrated residue was purified by a silica gel column chromatography to produce the title compound (0.04 g, yield 25~33%, cis:trans=2:1).

$^1$H NMR(400 MHz, $CDCl_3$) δ−0.11(s, 3H), 0.11(s, 3H), 0.93(s, 9H), 1.07(d, J=6.4 3H), 2.05(d, J=6.4 1H), 4.01~4.05 (m, 1H), 5.18(d, J=4.0, 1H), 7.20~7.56(m, 4H))

Preparation Example 55

Synthesis of 1-(2-chlorophenyl)-(R,S)-1,2-propanediol

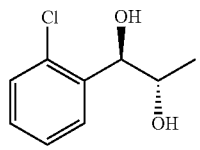

1-(2-chlorophenyl)-(R)-1-(t-butyldimethyl-siloxy)-(S)-2-propanol (10.38 g) obtained in Preparation Example 54 was dissolved in methanol ($CH_3OH$, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate ($MgSO_4$), filtrated, and concented under reduced pressure. The concentrated residue was purified by a silica gel column chromatography to produce the title compound (7.05 g, yield 60~90%).

$^1$H NMR(400 MHz, $CDCl_3$) δ1.07(d, J=6.8, 3H), 2.01(d, J=5.6, 1H), 2.61(s, 1H), 4.21~4.27(m, 1H), 5.24(d, J=3.6, 1H), 7.22~7.64(m, 4H)

Preparation Example 56

Synthesis of 1-(2-chlorophenyl)-(S,R)-1,2-propanediol

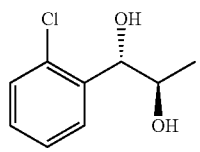

The substantially same method as described in Preparation Example 50~55 was conducted, except that (S)-2-chloromandelic acid was used instead of (R)-2-chloromandelic acid, to obtain the title compound (5.04 g, yield 84%).

$^1$H NMR(400 MHz, $CDCl_3$) δ1.07(d, J=6.8, 3H), 2.00(d, J=5.6, 1H), 2.54(d, J=3.6, 1H), 4.22~4.26(m, 1H), 5.25(t, J=3.2, 1H), 7.22~7.65(m, 4H)

Preparation Example 57

Synthesis of 1-(2,3-dichlorophenyl)-(S,S)-1,2-propanediol

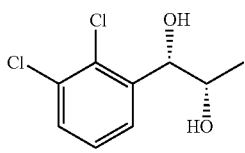

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H), 7.18~(m, 3H)

Preparation Example 58

Synthesis of 1-(2,3-dichlorophenyl)-(R,R)-1,2-propanediol

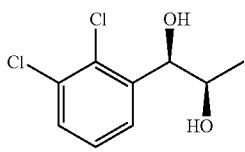

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H), 7.18~(m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

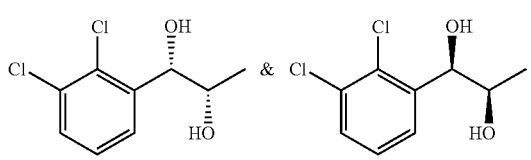

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H),4.47~4.54(m, 1H), 5.24(t, J=8.8 Hz, 1H), 7.18~(m, 3H)

Preparation Example 60

Synthesis of 1-(2-fluorophenyl)-trans-1-propene

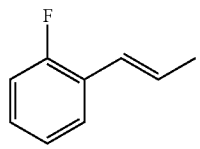

The substantially same method as described in Preparation Example 1 was conducted, except that 2-fluorobenzenaldehyde was used instead of 2-chlorobenzenealdehyde, to obtain the title compound (6.67 g, yield 61%).

$^1$H NMR(400 MHz, CDCl$_3$) δ1.94(d, J=6.8 Hz, 3H), 6.30~6.38(m, 1H), 6.57(d, J=16 Hz, 1H),7.00~7.41(m, 4H)

Preparation Example 61

Synthesis of 1-(2-fluorophenyl)-(S,S)-1,2-propanediol

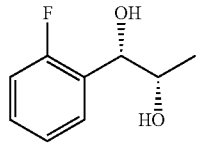

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

$^1$H NMR(400 MHz, CDCl$_3$) δ1.15(d, J=6.4 Hz, 3H), 2.43(d, J=3.6 Hz, 1H), 2.69(d, J=4.8 Hz, 1H),3.90~3.98(m, 1H), 4.78(dd, J=4.4, 7.2 Hz, 1H),7.04~7.50(m, 4H)

Preparation Example 62

Synthesis of 1-(2-fluorophenyl)-(R,R)-1,2-propanediol

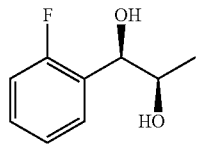

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

$^1$H NMR(400 MHz, CDCl$_3$) δ1.15(d, J=6.4 Hz, 3H), 2.43(d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 63

Synthesis of 2-iodobenzenealdehyde

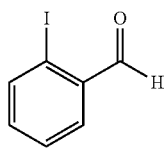

In a flask, 2-iodobenzyl alcohol (4 g, 17.09 mmol) was dissolved in dichloromethane (MC, 85 ml), and then, manganese oxide (MnO$_2$, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

$^1$H NMR(400 MHz, CDCl$_3$) δ7.30~7.99(m, 4H), 10.10(s, 1H)

Preparation Example 64

Synthesis of 1-(2-iodophenyl)-trans-1-propene

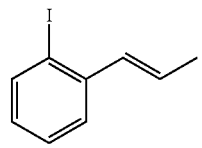

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

$^1$H NMR(400 MHz, CDCl$_3$) δ1.95(dd, J=6.8 Hz, 1.6 Hz, 3H),6.09~6.18(m, 1H), 6.60(dd, J=15.66 Hz, 1.8 Hz, 1H), 6.89~7.84(m, 4H)

Preparation Example 65

Synthesis of 1-(2-iodophenyl)-trans-1-butene

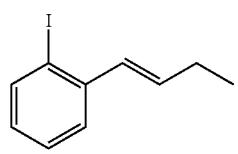

The substantially same method as described in Preparation Example 64 was conducted, except that 3-heptanone was used instead of 3-pentanone, to obtain the title compound (8.5 g, yield 75%).

$^1$H NMR(400 MHz, CDCl$_3$) δ1.46(t, J=7.6 Hz, 3H), 2.26~2.34(m, 2H), 6.17(dt, J=15.6 Hz, 6.6 Hz 1H), 6.57(d, J=15.6 Hz, 1H),6.89~7.85(m, 4H)

Preparation Example 66

Synthesis of 1-(2-iodophenyl)-(S,S)-1,2-propanediol

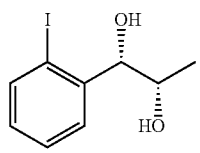

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR(400 MHz, CDCl$_3$) δ1.27(d, J=6.4 Hz, 3H), 2.26(br s, 1H), 2.74(br s, 1H), 3.99(t, J=6.0 Hz, 1H), 4.81(d, J=4.0 Hz, 1H),7.01~7.87(m, 4H)

Preparation Example 67

Synthesis of 1-(2-iodorophenyl)-(R,R)-1,2-propanediol

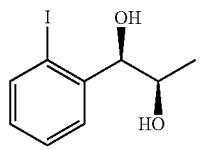

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR(400 MHz, CDCl$_3$) δ1.26(d, J=6.4 Hz, 3H), 2.35(br s, 1H), 2.85(br d, J=4.0 Hz, 1H), 3.98(t, J=6.2 Hz, 1H), 4.80(dd, J=5.0, 4.4 Hz, 1H),7.00~7.87(m, 4H)

Preparation Example 68

Synthesis of 1-(2-iodophenyl)-(S,S)-1,2-butanediol

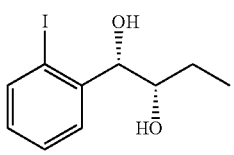

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR(400 MHz, CDCl$_3$) δ1.04(t, J=7.6 Hz, 3H), 1.60~1.71(m, 2H), 2.07(br s, 1H), 2.74(br s, 1H),3.71~3.76 (m, 1H), 4.87(d, J=4.8 Hz, 1H), 7.01~7.87(m, 4H)

Preparation Example 69

Preparation of 1-(2-chlorophenyl)-(S,S)-1,2-(Bis-trimethylsilanyloxy) propane

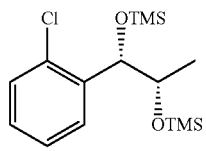

To a stirred solution of 1-(2-chlorophenyl)-(S,S)-1,2-propanediol (Preparation example 14, 67 g, 0.35 mol) in CH$_2$Cl$_2$ (670 ml) was added Et$_3$N (200 mL, 1.43 mol) and TMSCl (113.9 mL, 0.89 mol) at 0° C. under N$_2$. The reaction mixture was allowed to stir at 0° C. for 3 hr. The reaction mixture was quenched with H$_2$O (650 mL) at 0° C. The organic layer was separated and collected. The aqueous layer was extracted with CH$_2$Cl$_2$ (300 mL), dried over MgSO$_4$. Concentration under vacuum provided a crude product. 104.18 g (117.44%).

$^1$H NMR(400 MHz, CDCl$_3$) δ−0.053(s, 9H), 0.044(s, 9H), 1.15(d, J=5.6 Hz, 3H), 3.977~3.918(m, 1H), 4.973(d, J=6.4 Hz, 1H), 7.207~7.165(m, 1H), 7.321~7.245(m, 2H), 7.566~7.543(m, 1H)

Preparation Example 70

Preparation of 1-(2-chlorophenyl)-(R,R)-1,2-(Bis-trimethylsilanyloxy) propane

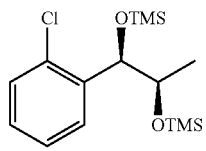

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

$^1$H NMR(400 MHz, CDCl$_3$) δ−0.053(s, 9H), 0.044(s, 9H), 1.15(d, J=5.6 Hz, 3H), 3.977~3.918(m, 1H), 4.973(d, J=6.4 Hz, 1H),7.21~7.54(m, 4H)

Preparation Example 71

Preparation of 1-(2-chlorophenyl)-1,2-(Bis-trimethylsilanyloxy) propane

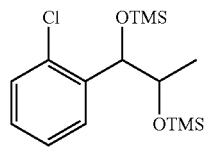

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).

$^1$H NMR(400 MHz, CDCl$_3$) δ−0.053(s, 9H), 0.044(s, 9H), 1.15(d, J=5.6 Hz, 3H), 3.977~3.918(m, 1H), 4.973(d, J6.4 Hz, 1H),7.21~7.54(m, 4H)

Preparation Example 72

Preparation of 1-(2-chlorophenyl)-(S,R)-1,2-(Bis-trimethylsilanyloxy) propane

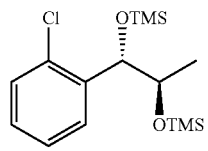

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).

$^1$H NMR(400 MHz, CDCl$_3$) δ−0.053(s, 9H), 0.044(s, 9H), 1.15(d, J=5.6 Hz, 3H), 3.977~3.918(m, 1H), 4.973(d, J=6.4 Hz, 1H),7.21~7.54(m, 4H)

Preparation Example 73

Preparation of 1-(2-chlorophenyl)-(R,S)-1,2-(Bis-trimethylsilanyloxy) propane

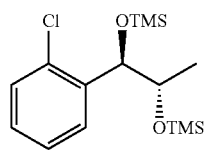

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).

¹H NMR(400 MHz, CDCl₃) δ−0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 74

Preparation of 1-(2-chlorophenyl)-(S,S)-1,2-(Bis-trimethylsilanyloxy) butane

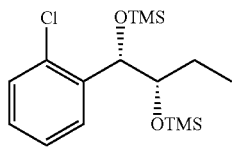

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).

¹H NMR(400 MHz, CDCl₃) δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 75

Preparation of 1-(2-chlorophenyl)-(R,R)-1,2-(Bis-trimethylsilanyloxy) butane

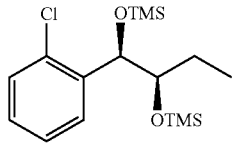

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).

¹H NMR(400 MHz, CDCl₃) δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 76

Preparation of 1-(2-chlorophenyl)-1,2-(Bis-trimethylsilanyloxy) butane

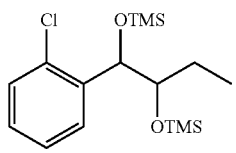

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).

¹H NMR(400 MHz, CDCl₃) δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 77

Preparation of 1-(2-chlorophenyl)-3-methyl-(S,S)-1,2-(Bis-trimethylsilanyloxy)-butane

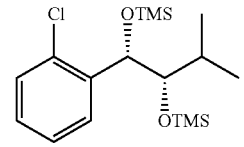

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%).

¹H NMR(400 MHz, CDCl₃) δ−0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 78

Preparation of 1-(2-chlorophenyl)-3-methyl-(R,R)-1,2-(Bis-trimethylsilanyloxy)-butane

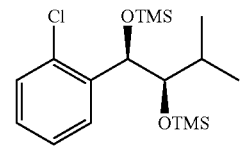

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

¹H NMR(400 MHz, CDCl₃) δ−0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 79

Preparation of 1-(2-chlorophenyl)-3-methyl-1,2-(Bis-trimethylsilanyloxy)-butane

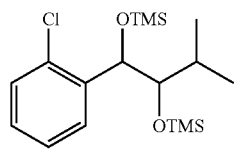

The substantially same method as described in Preparation Example 69 was conducted, except that 1-(2-chlorophenyl)-3-methyl-1,2-butanediol(Preparation example 22) was used instead of 1-(2-chlorophenyl)-(S,S)-1,2-propanediol(Preparation example 14) to obtain the title compound (2.8 g, yield 90~120%).
$^1$H NMR(400 MHz, CDCl$_3$) δ–0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 80

Preparation of 1-(2-chlorophenyl)-(S,S)-1,2-(Bis-trimethylsilanyloxy)-hexane

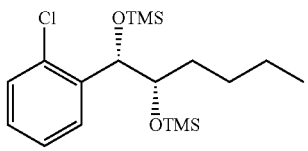

The substantially same method as described in Preparation Example 69 was conducted, except that 1-(2-chlorophenyl)-(S,S)-1,2-hexanediol(Preparation example 23) was used instead of 1-(2-chlorophenyl)-(S,S)-1,2-propanediol (Preparation example 14) to obtain the title compound (3.1 g, yield 90~120%).
$^1$H NMR(400 MHz, CDCl$_3$) δ–0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 81

Preparation of 1-(2-chlorophenyl)-(S,S)-1,2-(Bis-trimethylsilanyloxy)-hexane

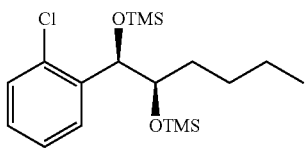

The substantially same method as described in Preparation Example 69 was conducted, except that 1-(2-chlorophenyl)-(R,R)-1,2-hexanediol(Preparation example 24) was used instead of 1-(2-chlorophenyl)-(S,S)-1,2-propanediol (Preparation example 14) to obtain the title compound (3.3 g, yield 90~120%).
$^1$H NMR(400 MHz, CDCl$_3$) δ–0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 82

Preparation of 1-(2-chlorophenyl)-(S,S)-1,2-(Bis-trimethylsilanyloxy)-hexane

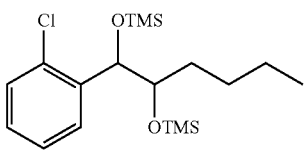

The substantially same method as described in Preparation Example 69 was conducted, except that 1-(2-chlorophenyl)-1,2-hexanediol(Preparation example 25) was used instead of 1-(2-chlorophenyl)-(S,S)-1,2-propanediol(Preparation example 14) to obtain the title compound (3.2 g, yield 90~120%).
$^1$H NMR(400 MHz, CDCl$_3$) δ–0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 83

Preparation of 1-(2,4-dichlorophenyl)-(S,S)-1,2-(Bis-trimethylsilanyloxy)-propane

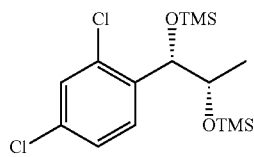

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).
$^1$H NMR(400 MHz, CDCl$_3$) δ–0.053(s, 9H), 0.044(s, 9H), 1.22(d, J=6.4 Hz, 3H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 84

Preparation of 1-(2,6-dichlorophenyl)-(S,S)-1,2-(Bis-trimethylsilanyloxy)-propane

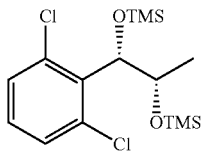

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

¹H NMR(400 MHz, CDCl₃) δ–0.053(s, 9H), 0.044(s, 9H), 1.10(d, J=6.4 Hz, 3H), 4.47~4.54(m, 1H), 5.24(t, J=8.8 Hz, 1H), 7.13~7.36(m, 3H)

Preparation Example 85

Preparation of 1-(2,3-dichlorophenyl)-(S,S)-1,2-(Bis-trimethylsilanyloxy)-propane

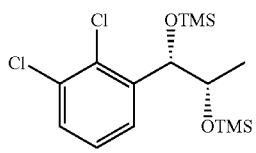

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

¹H NMR(400 MHz, CDCl₃) δ–0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 86

Preparation of 1-(2,4-dichlorophenyl)-(S,S)-1,2-(Bis-trimethylsilanyloxy)-butane

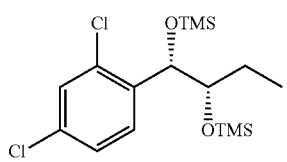

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

¹H NMR(400 MHz, CDCl₃) δ–0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 87

Preparation of 1-(2,6-dichlorophenyl)-(S,S)-1,2-(Bis-trimethylsilanyloxy)-butane

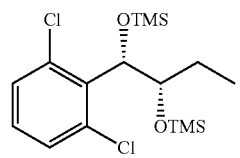

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

¹H NMR(400 MHz, CDCl₃) δ–0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 88

Preparation of 1-(2,4-dichlorophenyl)-3-methyl-(S,S)-1,2-(Bis-trimethylsilanyloxy)-butane

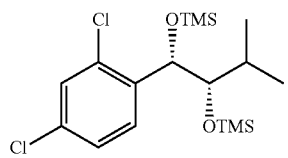

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

¹H NMR(400 MHz, CDCl₃) δ–0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 89

Preparation of 1-(2,6-dichlorophenyl)-3-methyl-(S,S)-1,2-(Bis-trimethylsilanyloxy)-butane

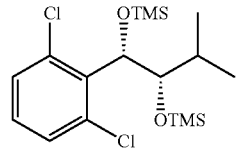

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-

1,2-propanediol (Preparation example 14) to obtain the title compound (3.3 g, yield 90~120%).

$^1$H NMR(400 MHz, CDCl$_3$) δ−0.053(s, 9H), 0.044(s, 9H), 1.00(d, J=6.8 Hz, 6H), 1.60~1.65(m, 1H), 4.13~4.18 (m, 1H), 5.36(t, J=7.6 Hz, 1H), 7.17~7.35(m, 3H)

Preparation Example 90

Preparation of 1-(2,4-dichlorophenyl)-(S,S)-1,2-(Bis-trimethylsilanyloxy)-hexane

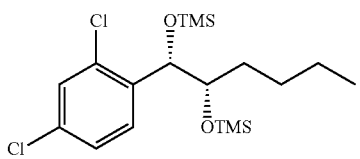

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$) δ−0.053(s, 9H), 0.044(s, 9H), 0.89~0.93(m, 3H), 1.30~1.39(m, 2H), 1.49~1.52(m, 2H), 1.56~1.6(m, 2H), 3.72~3.77(m, 1H), 4.98(t, J=4.8 Hz, 1H), 7.28~7.50(m, 3H)

Preparation Example 91

Preparation of 1-(2,6-dichlorophenyl)-(S,S)-1,2-(Bis-trimethylsilanyloxy)-hexane

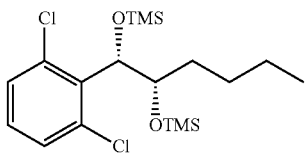

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$) δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 92

Preparation of 1-(2,4-dichlorophenyl)-(R,R)-1,2-(Bis-trimethylsilanyloxy)-propane

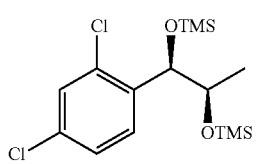

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR(400 MHz, CDCl$_3$) δ−0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 93

Preparation of 1-(2,6-dichlorophenyl)-(R,R)-1,2-(Bis-trimethylsilanyloxy)-propane

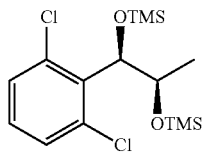

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR(400 MHz, CDCl$_3$) δ−0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 94

Preparation of 1-(2,3-dichlorophenyl)-(R,R)-1,2-(Bis-trimethylsilanyloxy)-propane

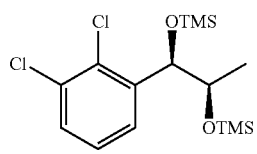

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR(400 MHz, CDCl$_3$) δ−0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 95

Preparation of 1-(2,4-dichlorophenyl)-(R,R)-1,2-(Bis-trimethylsilanyloxy)-butane

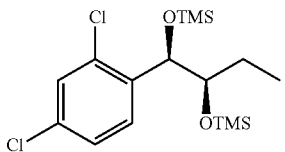

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$) δ−0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 96

Preparation of 1-(2,6-dichlorophenyl)-(R,R)-1,2-(Bis-trimethylsilanyloxy)-butane

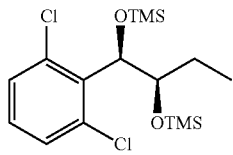

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$) δ−0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 97

Preparation of 1-(2,4-dichlorophenyl)-3-methyl-(R,R)-1,2-(Bis-trimethylsilanyloxy)-butane

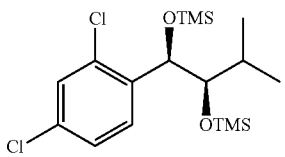

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

$^1$H NMR(400 MHz, CDCl$_3$) δ−0.053(s, 9H), 0.044(s, 9H), 1.00(d, J=6.8 Hz, 6H), 1.60~1.65(m, 1H), 4.13~4.18 (m, 1H), 5.36(t, J=7.6 Hz, 1H), 7.30~7.53(m, 3H)

Preparation Example 98

Preparation of 1-(2,6-dichlorophenyl)-3-methyl-(R,R)-1,2-(Bis-trimethylsilanyloxy)-butane

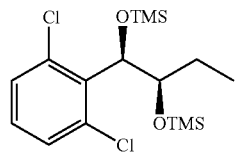

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).

$^1$H NMR(400 MHz, CDCl$_3$) δ−0.053(s, 9H), 0.044(s, 9H), 1.00(d, J=6.8 Hz, 6H), 1.60~1.65(m, 1H), 4.13~4.18 (m, 1H), 5.36(t, J=7.6 Hz, 1H), 7.17~7.35(m, 3H)

Preparation Example 99

Preparation of 1-(2,4-dichlorophenyl)-(R,R)-1,2-(Bis-trimethylsilanyloxy)-hexane

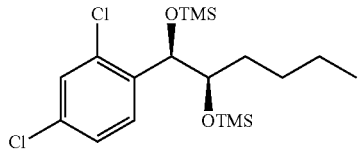

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$) δ−0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 100

Preparation of 1-(2,6-dichlorophenyl)-(R,R)-1,2-(Bis-trimethylsilanyloxy)-hexane

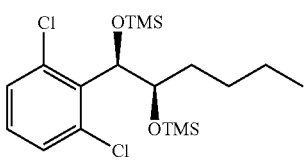

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

¹H NMR(400 MHz, CDCl₃) δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 101

Preparation of 1-(2,4-dichlorophenyl)-1,2-(Bis-trimethylsilanyloxy)-propane

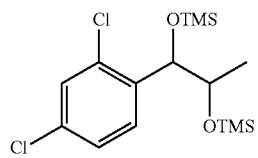

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

¹H NMR(400 MHz, CDCl₃) δ−0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 102

Preparation of 1-(2,6-dichlorophenyl)-1,2-(Bis-trimethylsilanyloxy)-propane

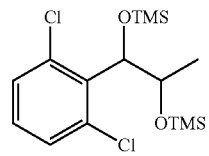

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

¹H NMR(400 MHz, CDCl₃) δ−0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 103

Preparation of 1-(2,3-dichlorophenyl)-1,2-(Bis-trimethylsilanyloxy)-propane

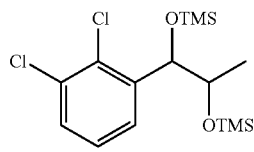

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).

¹H NMR(400 MHz, CDCl₃) δ−0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 104

Preparation of 1-(2,4-dichlorophenyl)-1,2-(Bis-trimethylsilanyloxy)-butane

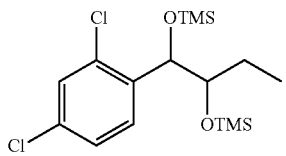

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

¹H NMR(400 MHz, CDCl₃) δ−0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 105

Preparation of 1-(2,6-dichlorophenyl)-1,2-(Bis-trimethylsilanyloxy)-butane

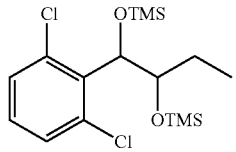

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

¹H NMR(400 MHz, CDCl₃) δ−0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 106

Preparation of 1-(2,4-dichlorophenyl)-3-methyl-1,2-(Bis-trimethylsilanyloxy)-butane

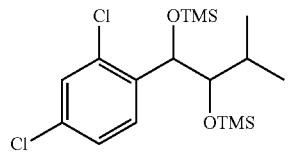

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).

¹H NMR(400 MHz, CDCl₃) δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 107

Preparation of 1-(2,6-dichlorophenyl)-3-methyl-1,2-(Bis-trimethylsilanyloxy)-butane

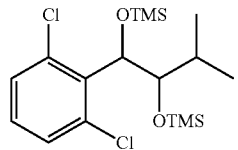

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).

¹H NMR(400 MHz, CDCl₃) δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 108

Preparation of 1-(2,4-dichlorophenyl)-1,2-(Bis-trimethylsilanyloxy)-hexane

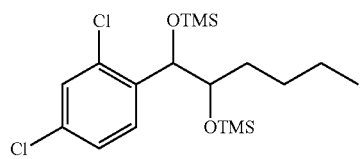

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

¹H NMR(400 MHz, CDCl₃) δ−0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 109

Preparation of 1-(2,6-dichlorophenyl)-1,2-(Bis-trimethylsilanyloxy)-hexane

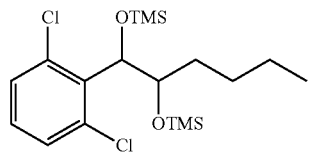

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

¹H NMR(400 MHz, CDCl₃) δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 110

Preparation of 1-(2-fluorophenyl)-(S,S)-1,2-(Bis-trimethylsilanyloxy)-propane

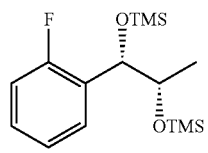

The substantially same method as described in Preparation Example 69 was conducted, except that 1-(2-fluorophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

¹H NMR(400 MHz, CDCl₃) δ−0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 111

Preparation of 1-(2-fluorophenyl)-(R,R)-1,2-(Bis-trimethylsilanyloxy)-propane

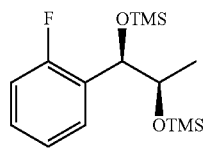

The substantially same method as described in Preparation Example 69 was conducted, except that 1-(2-fluorophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

$^1$H NMR(400 MHz, CDCl$_3$) δ−0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 112

Preparation of 1-(2-iodophenyl)-(S,S)-1,2-(Bis-trimethylsilanyloxy)-propane

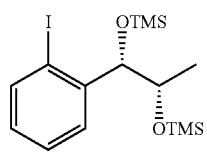

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%). 15 $^1$H NMR(400 MHz, CDCl$_3$) δ−0.053 (s, 9H), 0.044(s, 9H), 1.27(d, J=6.4 Hz, 3H), 3.99(t, J=6.0 Hz, 1H), 4.81(d, J=4.0 Hz, 1H), 7.01~7.87(m, 4H)

Preparation Example 113

Preparation of 1-(2-iodophenyl)-(R,R)-1,2-(Bis-trimethylsilanyloxy)-propane

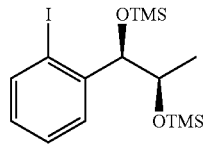

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$) δ−0.053(s, 9H), 0.044(s, 9H), 1.26(d, J=6.4 Hz, 3H), 3.98(t, J=6.2 Hz, 1H), 4.88(d, J=4.4 Hz, 1H), 7.00~7.87(m, 4H)

Preparation Example 114

Preparation of 1-(2-iodophenyl)-(S,S)-1,2-(Bis-trimethylsilanyloxy)-butane

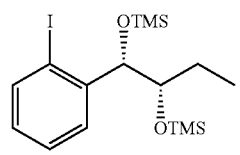

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$) δ−0.053(s, 9H), 0.044(s, 9H), 1.04(t, J=7.6 Hz, 3H), 1.60~1.71(m, 2H), 3.71~3.76(m, 1H), 4.87(d, J=4.8 Hz, 1H), 7.01~7.87(m, 4H)

Example 1

Preparation of 1-(2-chlorophenyl)-(S)-1-hydroxypropyl-(S)-2-carbamate (1)

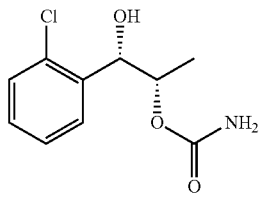

To a stirred solution of crude 1-(2-chlorophenyl)-(S,S)-1,2-(Bis-trimethylsilanyloxy) propane (preparation example 69, 104 g, 0.31 mol) in toluene (670 mL) was added by Chlorosulfonyl isocynate (62.5 mL, 0.71 mol) at 0° C. The reaction mixture was stirred for 2 hr. The reaction mixture was quenched with ice water and then was stirred by additional cold H$_2$O (500 mL) for 2 hr. After separation of organic layer, the aqueous was adjusted pH2~3 with sat. NaHCO$_3$(400 mL) and extracted with EtOAc (300 mL×3). The EtOAc layer was washed with sat. NaHCO$_3$ (500 mL) and H$_2$O (500 mL). The organic phase was treated with Charcoal for 1.5 hr. The organic phase was filtered with Cellite, dried over MgSO$_4$. Filterion and concentration under vacuum provided the title compound of white solid (yield 85%(71.1 g), ee=99.9% MP=83~84° C., [α]$_D$=+57.8 (c=0.25, MeOH))

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

$^{13}$C NMR(100 MHz, CDCl$_3$) δ16.4, 73.1, 75.0, 127.0, 128.4, 129.1, 129.5, 132.7, 138.0, 156.6

Example 2

Preparation of 1-(2-chlorophenyl)-(R)-1-hydroxy-propyl-(R)-2-carbamate (2)

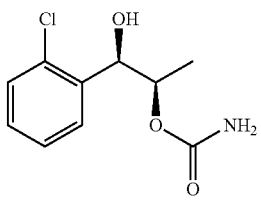

The substantially same method as described in Example 1 was conducted, except that 1-(2-chlorophenyl)-(R,R)-1,2-(Bis-trimethylsilanyloxy) propane (Preparation example 70) was used instead of 1-(2-chlorophenyl)-(S,S)-1,2-(Bis-trimethylsilanyloxy) propane (Preparation example 69) to obtain the title compound (5.7 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 3

Preparation of 1-(2-chlorophenyl)-1-hydroxypropyl-2-carbamate (3)

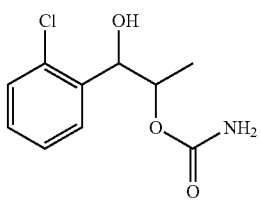

The substantially same method as described in Example 1 was conducted, except that 1-(2-chlorophenyl)-1,2-(Bis-trimethylsilanyloxy) propane (Preparation example 71) was used instead of 1-(2-chlorophenyl)-(S,S)-1,2-(Bis-trimethylsilanyloxy) propane (Preparation example 69) to obtain the title compound (3.8 g, yield 60~90%).

$^1$H NMR(400 MHz, CDCl$_3$) δ1.24(d, J=6.4, 3H), 2.91(d, J=4.8, 1H), 4.68 (br s, 2H), 5.06~5.09(m, 1H), 5.18~5.21(m, 1H), 7.23~7.39(m, 3H), 7.55(dd, J=1.6, J=7.8, 1H)

Example 4

Preparation of 1-(2-chlorophenyl)-(S)-1-hydroxy-propyl-(R)-2-carbamate (4)

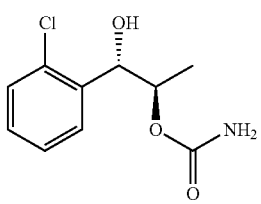

The substantially same method as described in Example 1 was conducted, except that 1-(2-chlorophenyl)-(S,R)-1,2-(Bis-trimethylsilanyloxy) propane (Preparation example 72) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 5

Preparation of 1-(2-chlorophenyl)-(R)-1-hydroxy-propyl-(S)-2-carbamate (5)

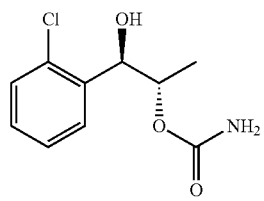

The substantially same method as described in Example 1 was conducted, except that 1-(2-chlorophenyl)-(R,S)-1,2-(Bis-trimethylsilanyloxy) propane (Preparation example 73) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 6

Preparation of 1-(2-chlorophenyl)-(S)-1-hydroxybu-tyl-(S)-2-carbamate (6)

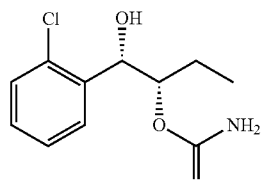

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400 MHz, CDCl$_3$) δ0.96(t, J=7.4 Hz, 3H), 1.57~1.73(m, 2H), 3.01(d, J=5.6 Hz, 1H), 4.74(br s, 2H), 4.95(dt, J=7.2, 8.8 Hz, 1H), 5.23(t, J=5.6 Hz, 1H), 7.22~7.54 (m, 4H)

Example 7

Synthesis of 1-(2-chlorophenyl)-(R)-1-hydroxybutyl-(R)-2-carbamate (7)

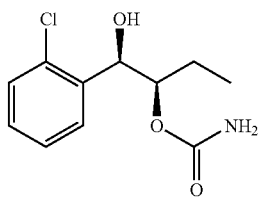 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ 0.94(t, J=7.4 Hz, 3H), 1.53~1.73(m, 2H), 2.92(s, 1H), 4.78(br s, 2H), 4.91~4.96(m, 1H), 5.22(d, J=5.5 Hz, 1H), 7.20~7.54(m, 4H)

Example 8

Synthesis of 1-(2-chlorophenyl)-1-hydroxybutyl-2-carbamate (8)

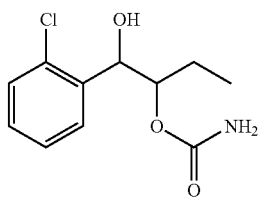 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR(400 MHz, CDCl$_3$) δ 0.97(t, J=7 Hz, 3H), 1.58~1.74(m, 2H), 2.94(d, J=6 Hz, 1H), 4.69(br s, 2H), 4.94~4.99(m, 1H), 5.24(t, J=6 Hz, 1H), 7.23~7.56(m, 4H)

Example 9

Synthesis of 1-(2-chlorophenyl)-(S)-1-hydroxy-3-methyl-butyl-(S)-2-carbamate (9)

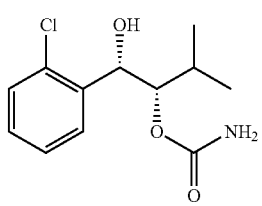 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.01(d, J=6.4 Hz, 3H), 1.09(d, J=6.8 Hz, 3H), 2.06(m, 1H), 2.75(d, J=6.8 Hz, 1H), 4.58(br s, 2H), 4.85~4.88(m, 1H), 5.34~5.37(m, 1H), 7.22~7.33(m, 2H), 7.35~7.37(m, 1H), 7.51~7.53(m, 1H)

Example 10

Synthesis of 1-(2-chlorophenyl)-(R)-1-hydroxy-3-methyl-butyl-(R)-2-carbamate (10)

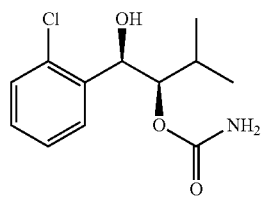 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.01(d, J=6.8 Hz, 3H), 1.09(d, J=6.8 Hz, 3H), 2.06(m, 1H), 2.73(d, J=6.8 Hz, 1H), 4.57(br s, 2H), 4.85~4.88(m, 1H), 5.34~5.37(m, 1H), 7.24~7.30(m, 2H), 7.35~7.37(m, 1H), 7.51~7.53(m, 1H)

Example 11

Synthesis of 1-(2-chlorophenyl)-1-hydroxy-3-methyl-butyl-2-carbamate (11)

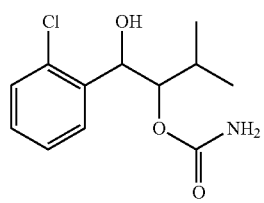 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.00(d, J=6.4 Hz, 3H), 1.09(d, J=6.4 Hz, 3H), 2.08(m, 1H), 2.76(d, J=6.0 Hz, 1H), 4.59(br s, 2H), 4.87(dd, J=7.2 Hz, 4.4 Hz, 1H), 5.36(t, J=4.6, 1H), 7.23~7.54(m, 4H)

Example 12

Synthesis of 1-(2-chlorophenyl)-(S)-1-hydroxy-hexyl-(S)-2-carbamate (12)

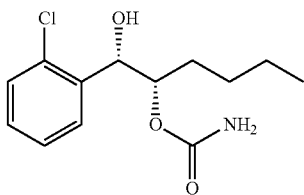

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR(400 MHz, CDCl$_3$) δ0.88(t, J=7 Hz, 3H), 1.33~1.42(m, 4H), 1.53~1.71(m, 2H), 2.89(d, J=5.6 Hz, 1H) 4.64(br s, 2H), 5.04(dt, J=5.0, 9.0 Hz, 1H), 5.20(t, J=5.6 Hz, 1H), 7.23~7.55(m, 4H)

Example 13

Synthesis of 1-(2-chlorophenyl)-(R)-1-hydroxy-hexyl-(R)-2-carbamate (13)

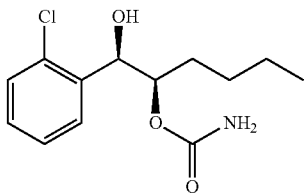 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ0.89(dd, J=5 Hz, 3H), 1.28~1.43(m, 4H), 1.52~1.58(m, 1H), 1.65~1.72(m, 1H), 2.90(d, J=6 Hz, 1H), 4.64(br s, 2H), 5.01~5.06(m, 1H), 5.22(t, J=6 Hz, 1H), 7.22~7.56(m, 4H)

Example 14

Synthesis of 1-(2-chlorophenyl)-1-hydroxyhexyl-2-carbamate (14)

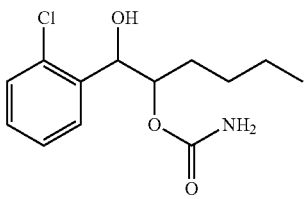 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR(400 MHz, CDCl$_3$) δ 0.88(dd, J=5 Hz, 3H), 1.31~1.43(m, 4H), 1.63~1.70(m, 1H), 1.52~1.60(m, 1H), 3.06(d, J=6 Hz, 1H), 4.75(br s, 2H), 5.00~5.05(m, 1H), 5.21(t, J=6 Hz, 1H), 7.22~7.55(m, 4H)

Example 15

Synthesis of 1-(2-chlorophenyl)-(S)-1-hydroxypropyl-(S)-2-N-methylcarbamate (15)

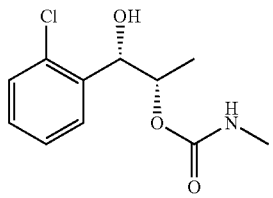 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH$_3$NH$_2$, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO$_4$), filtrated, and concented under reduced pressure. The concentrated residue was purified by a silica gel column chromatography, to obtain the title compound (1.6 g, yield 51%).

$^1$H NMR(400 MHz, CDCl$_3$) δ1.03~1.25(m, 3H), 2.76(s, 3H), 3.34(s, 1H), 4.80(br s 1H), 5.04(t, J=12.5 Hz, 1H), 5.14(s, 1H), 7.20~7.53(m, 4H)

Example 16

Synthesis of 1-(2-chlorophenyl)-(S)-1-hydroxypropyl-(S)-2-N-propylcarbamate (16)

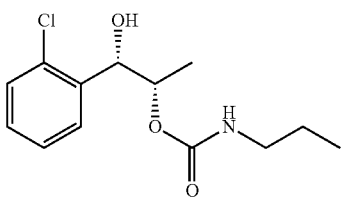 [SMILES: CCCNC(=O)O[C@@H](C)[C@@H](O)c1ccccc1Cl]

The substantially same method as described in Example 15 was conducted, except that propylamine was used instead of methylamine solution ($CH_3NH_2$ in EtOH), to obtain the title compound (0.79 g, yield 25%).

$^1$H NMR(400 MHz, $CDCl_3$) δ0.90(t, J=6.8 Hz, 3H), 1.20(d, J=5.96 Hz, 3H), 1.49(dd, J=14.2 Hz, 2H), 3.11(d, J=6.28 Hz, 2H), 3.34(s, 1H), 4.84(br s, 1H), 5.05(t, J=5.88 Hz, 1H), 5.14(s, 1H), 7.22~7.53(m, 4H)

Example 17

Synthesis of 1-(2-chlorophenyl)-(S)-1-hydroxypropyl-(R)-2-N-isopropylcarbamate (17)

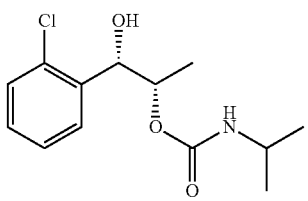

The substantially same method as described in Example 15 was conducted, except that isopropylamine was used instead of methylamine solution ($CH_3NH_2$ in EtOH), to obtain the title compound (1.5 g, yield 41%).

$^1$H NMR(400 MHz, $CDCl_3$) δ1.14(dd, J=6.5 Hz, 6H), 1.19(d, J=6.4 Hz, 3H), 3.21(s, 1H),3.73~3.82(m, 1H), 4.59 (br s, 1H),5.01~5.07(m, 1H), 5.14(t, J=5.8 Hz, 1H), 7.20~7.53(m, 4H)

Example 18

Synthesis of 1-(2-chlorophenyl)-(S)-1-hydroxypropyl-(R)-2-N-cyclopropylcarbamate (18)

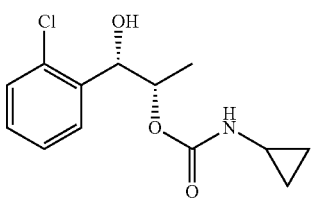 [SMILES: C[C@H](OC(=O)NC1CC1)[C@@H](O)c1ccccc1Cl]

The substantially same method as described in Example 15 was conducted, except that cyclopropylamine was used instead of methylamine solution ($CH_3NH_2$ in EtOH), to obtain the title compound (2.2 g, yield 43%).

$^1$H NMR(400 MHz, $CDCl_3$) δ0.50~0.56(m, 2H), 0.74(d, J=7.21 Hz, 2H), 1.25(s, 3H), 2.56~2.61(m, 1H), 3.72(s, 1H), 4.98(br s, 1H), 5.05~5.11(m, 1H), 7.16(s, 1H), 7.23~7.54(m, 4H)

Example 19

Synthesis of 1-(2-chlorophenyl)-(S)-1-hydroxypropyl-(R)-2-N-cyclohexyl carbamate (19)

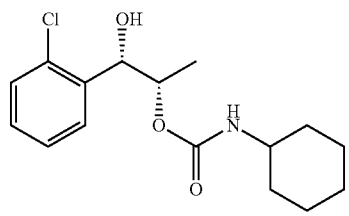 [SMILES: C[C@H](OC(=O)NC1CCCCC1)[C@@H](O)c1ccccc1Cl]

The substantially same method as described in Example 15 was conducted, except that cyclohexylamine was used instead of methylamine solution ($CH_3NH_2$ in EtOH), to obtain the title compound (1.1 g, yield 26%).

$^1$H NMR(400 MHz, $CDCl_3$) δ1.06~1.40(m, 7H), 1.56~1.61(m, 2H), 1.69~1.71(m, 2H), 1.87~1.94(m, 2H), 3.19(d, J=4.32 Hz, 1H), 3.45(s, 1H), 4.64(br s 1H), 5.02~5.07(m, 1H), 5.14(t, J=6.08 Hz, 1H) 7.20~7.53(m, 4H)

Example 20

Synthesis of 1-(2-chlorophenyl)-(S)-1-hydroxypropyl-(S)-2-N-benzyl carbamate (20)

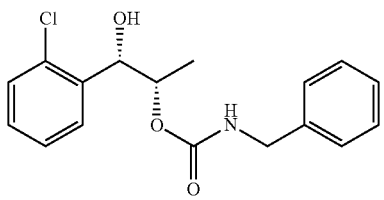 [SMILES: C[C@H](OC(=O)NCc1ccccc1)[C@@H](O)c1ccccc1Cl]

The substantially same method as described in Example 15 was conducted, except that benzylamine was used instead of methylamine solution ($CH_3NH_2$ in EtOH), to obtain the title compound (1.2 g, yield 18%).

$^1$H NMR(400 MHz, $CDCl_3$) δ 1.27(d, J=10 Hz, 3H), 3.12(d, J=5 Hz, 1H), 4.37(d, J=6 Hz, 2H), 5.12~5.19(m, 3H), 7.15~7.56(m, 9H)

Example 21

Synthesis of 1-(2-chlorophenyl)-(S)-1-hydroxypropyl-(S)-2-N-bicyclo[2,2,1]heptanescarbamate (21)

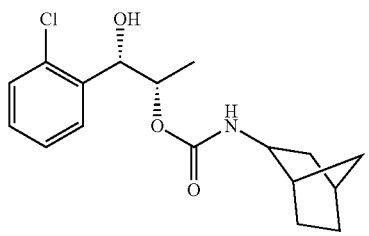 [SMILES: C[C@H](OC(=O)NC1CC2CCC1C2)[C@@H](O)c1ccccc1Cl]

The substantially same method as described in Example 15 was conducted, except that 2-aminonorbornane was used instead of methylamine solution (CH$_3$NH$_2$ in EtOH), to obtain the title compound (1.7 g, yield 32%).

$^1$H NMR(400 MHz, CDCl$_3$) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 22

Synthesis of 1-(2-chlorophenyl)-(R)-1-hydroxypropyl-(R)-2-N-methylcarbamate (22)

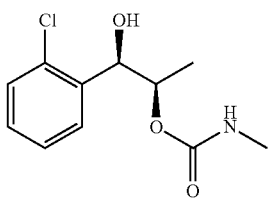 [SMILES: CNC(=O)O[C@H](C)[C@H](O)c1ccccc1Cl]

The substantially same method as described in Example 15 was conducted, except that 1-(2-chlorophenyl)-(R,R)-1,2-propanediol (Preparation example 15) was used instead of 1-(2-chlorophenyl)-(S,S)-1,2-propanediol (Preparation example 14), to obtain the title compound (3.36 g, yield 60%).

$^1$H NMR(400 MHz, CDCl$_3$) δ 1.20(d, J=6.8 Hz, 3H), 2.80(d, J=4.8 Hz, 3H), 3.20(d, J=4.4 Hz, 1H), 4.75(br s, 1H), 5.03~5.09(m, 1H), 5.14~5.17(m, 1H), 7.22~7.55(m, 4H)

Example 23

Synthesis of 1-(2-chlorophenyl)-(R)-1-hydroxypropyl-(R)-2-N-propylcarbamate (23)

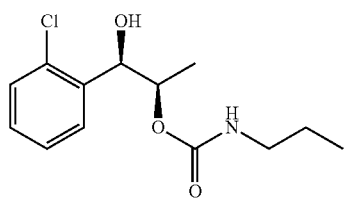 [SMILES: CCCNC(=O)O[C@H](C)[C@H](O)c1ccccc1Cl]

The substantially same method as described in Example 22 was conducted, except that propylamine was used instead of methylamine solution (CH$_3$NH$_2$ in EtOH), to obtain the title compound (3.1 g, yield 53%).

$^1$H NMR(400 MHz, CDCl$_3$) δ0.92(t, J=7.6 Hz, 3H), 1.21(d, J=6.4 Hz, 3H), 1.51(m, 2H), 3.09~3.14(m, 2H), 3.28(d, J=4.4 Hz, 1H), 4.82(br s, 1H), 5.03~5.09(m, 1H), 5.14~5.17(m, 1H), 7.22~7.55(m, 4H)

Example 24

Synthesis of 1-(2-chlorophenyl)-(R)-1-hydroxypropyl-(R)-2-N-isopropylcarbamate (24)

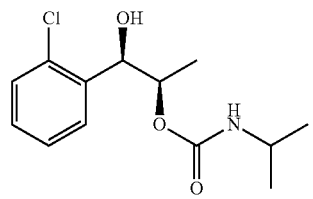 [SMILES: CC(C)NC(=O)O[C@H](C)[C@H](O)c1ccccc1Cl]

The substantially same method as described in Example 22 was conducted, except that isopropylamine was used instead of methylamine solution (CH$_3$NH$_2$ in EtOH), to obtain the title compound (0.16 g, yield 27%).

$^1$H NMR(400 MHz, CDCl$_3$) δ0.88~1.16(m, 6H), 1.19~1.26(m, 3H), 3.34(s, 1H), 3.71~3.78(m, 1H), 4.62(br s, 1H), 5.03(t, J=5.8 Hz, 1H), 5.13(d, J=4.9 Hz, 1H), 7.20~7.53(m, 4H)

Example 25

Synthesis of 1-(2-chlorophenyl)-(R)-1-hydroxypropyl-(R)-2-N-cyclopropylcarbamate (25)

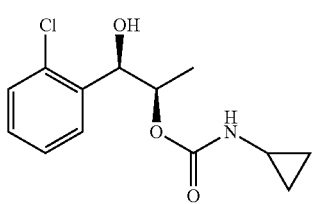 [SMILES: C[C@@H](OC(=O)NC1CC1)[C@H](O)c1ccccc1Cl]

The substantially same method as described in Example 22 was conducted, except that cyclopropylamine was used instead of methylamine solution (CH$_3$NH$_2$ in EtOH), to obtain the title compound (3.7 g, yield 60%).

$^1$H NMR(400 MHz, CDCl$_3$) δ0.49~0.54(m, 2H), 0.74(d, J=7.2 Hz, 2H), 1.22(s, 3H), 2.55~2.60(m, 1H), 3.16(s, 1H), 5.00(s, 1H), 5.04~5.11(m, 1H), 5.16(s, 1H), 7.23~7.54(m, 4H)

Example 26

Synthesis of 1-(2-chlorophenyl)-(R)-1-hydroxypropyl-(R)-2-N-cyclohexyl carbamate (26)

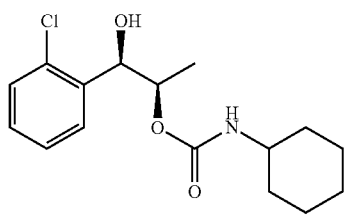 [SMILES: C[C@@H](OC(=O)NC1CCCCC1)[C@H](O)c1ccccc1Cl]

The substantially same method as described in Example 22 was conducted, except that cyclohexylamine was used instead of methylamine solution ($CH_3NH_2$ in EtOH), to obtain the title compound (1.9 g, yield 28%).

$^1$H NMR(400 MHz, CDCl$_3$) δ1.05~1.38(m, 8H), 1.58~1.70(m, 3H), 1.85~1.95(m, 2H), 3.39~3.47(m, 1H), 3.56(s, 1H), 4.79(br s, 1H), 5.01~5.07(m, 1H), 5.14(t, J=5.2 Hz, 1H), 7.20~7.54(m, 4H)

Example 27

Synthesis of 1-(2-chlorophenyl)-(R)-1-hydroxypropyl-(R)-2-N-benzylcarbamate (27)

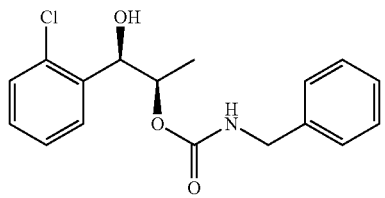 [SMILES: C[C@@H](OC(=O)NCc1ccccc1)[C@H](O)c1ccccc1Cl]

The substantially same method as described in Example 22 was conducted, except that benzylamine was used instead of methylamine solution ($CH_3NH_2$ in EtOH), to obtain the title compound (0.52 g, yield 19%).

$^1$H NMR(400 MHz, CDCl$_3$) δ1.25(d, J=6 Hz, 3H), 1.64(s, 1H), 3.13(d, J=4.4 Hz, 1H), 4.37(d, J=5.6 Hz, 2H), 5.12~5.19(m, 2H), 7.23~7.55(m, 9H)

Example 28

Synthesis of 1-(2-chlorophenyl)-(R)-1-hydroxypropyl-(R)-2-N-bicyclo[2,2,1]heptanecarbamate (28)

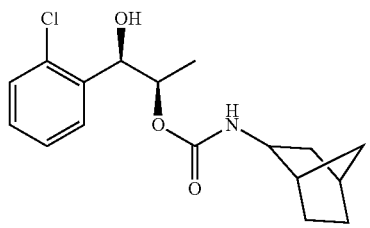 [SMILES: C[C@@H](OC(=O)NC1CC2CCC1C2)[C@H](O)c1ccccc1Cl]

The substantially same method as described in Example 22 was conducted, except that 2-aminonorbornane was used instead of methylamine solution ($CH_3NH_2$ in EtOH), to obtain the title compound (1.7 g, yield 20~50%).

$^1$H NMR(400 MHz, CDCl$_3$) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 29

Synthesis of 1-(2-chlorophenyl)-1-hydroxypropyl-2-N-methylcarbamate(29)

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

$^1$H NMR(400 MHz, CDCl$_3$) δ 1.21(d, J=6 Hz, 3H), 2.81(d, J=5 Hz, 3H), 3.14(d, J=4 Hz, 1H), 4.72(br s, 1H), 5.07(dd, J=6 Hz, 1H), 5.16(t, J=6 Hz, 1H), 7.22~7.56(m, 4H)

Example 30

Synthesis of 1-(2-chlorophenyl)-1-hydroxypropyl-2-N-propylcarbamate (30)

The substantially same method as described in Example 29 was conducted, except that propylamine was used instead of methylamine solution ($CH_3NH_2$ in EtOH), to obtain the title compound (1.0 g, yield 17%).

$^1$H NMR(400 MHz, CDCl$_3$) δ 0.92(t, J=7 Hz, 3H), 1.21(d, J=6 Hz, 3H), 1.53(dd, J=7 Hz, 2H), 3.13(dd, J=7 Hz, 2H), 3.28(d, 1H), 4.82(s, 1H), 5.06(dd, J=7 Hz, 1H), 5.16(t, J=5 Hz, 1H), 7.21~7.56(m, 4H)

Example 31

Synthesis of 1-(2-chlorophenyl)-1-hydroxypropyl-2-N-isopropylcarbamate (31)

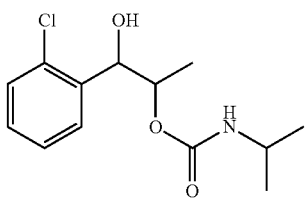 [SMILES: CC(C)NC(=O)OC(C)C(O)c1ccccc1Cl]

The substantially same method as described in Example 29 was conducted, except that isopropylamine was used instead of methylamine solution (CH₃NH₂ in EtOH), to obtain the title compound (0.54 g, yield 16%).

¹H NMR(400 MHz, CDCl₃) δ 1.16(dd, J=6 Hz, 6H), 1.21(d, J=6 Hz, 3H), 3.23(d, J=6 Hz, 1H), 3.75~3.84(m, 1H), 4.61(br s, 1H), 5.06(t, J=6 Hz, 1H), 5.16(t, J=6 Hz, 1H), 7.22~7.56(m, 4H)

Example 32

Synthesis of 1-(2-chlorophenyl)-1-hydroxypropyl-2-N-cyclopropylcarbamate (32)

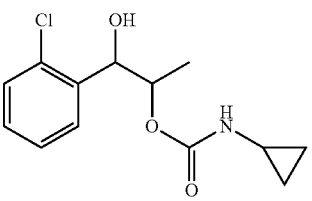 [SMILES: CC(OC(=O)NC1CC1)C(O)c1ccccc1Cl]

The substantially same method as described in Example 29 was conducted, except that cyclopropylamine was used instead of methylamine solution (CH₃NH₂ in EtOH), to obtain the title compound (1.0 g, yield 17%).

¹H NMR(400 MHz, CDCl₃) δ 0.50(t, J=6 Hz, 2H), 0.77(t, J=3 Hz, 2H), 1.12(d, J=7 Hz, 3H), 2.53~2.59(m, 1H), 3.22(d, J=4 Hz, 1H), 5.08(dd, J=6 Hz, 1H), 5.15(s, 1H), 7.22~7.55(m, 4H)

Example 33

Synthesis of 1-(2-chlorophenyl)-1-hydroxypropyl-2-N-cyclohexylcarbamate (33)

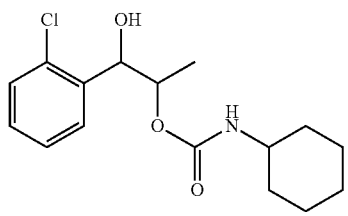 [SMILES: CC(OC(=O)NC1CCCCC1)C(O)c1ccccc1Cl]

The substantially same method as described in Example 29 was conducted, except that cyclohexylamine was used instead of methylamine solution (CH₃NH₂ in EtOH), to obtain the title compound (2.2 g, yield 33%).

¹H NMR(400 MHz, CDCl₃) δ 1.07~1.17(m, 3H), 1.21(d, J=6 Hz, 3H), 1.29~1.42(m, 3H), 1.72(dd, J=6 Hz, 2H), 1.92(dd, J=6 Hz, 2H), 3.26(d, J=4 Hz, 1H), 3.46(t, J=4 Hz, 1H), 4.68(d, J=6 Hz, 1H), 5.07(dd, J=6 Hz, 1H), 5.16(t, J=6 Hz, 1H), 7.22~7.55(m, 4H)

Example 34

Synthesis of 1-(2-chlorophenyl)-1-hydroxypropyl-2-N-benzylcarbamate (34)

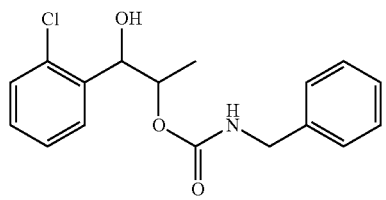 [SMILES: CC(OC(=O)NCc1ccccc1)C(O)c1ccccc1Cl]

The substantially same method as described in Example 29 was conducted, except that benzylamine was used instead of methylamine solution (CH₃NH₂ in EtOH), to obtain the title compound (1.3 g, yield 19%).

¹H NMR(400 MHz, CDCl₃) δ 1.25(d, J=6 Hz, 3H), 3.16(d, J=4 Hz, 1H), 4.36(d, J=6 Hz, 2H), 5.14(dd, J=6 Hz, 3H), 7.23~7.56(m, 9H), yield: 19%(1.3 g)

Example 35

Synthesis of 1-(2-chlorophenyl)-1-hydroxypropyl-2-N-bicyclo[2,2,1]heptanecarbamate (35)

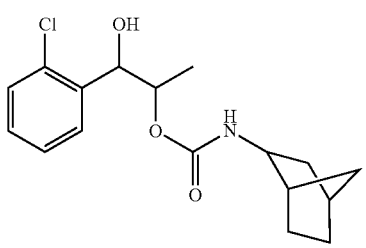 [SMILES: CC(OC(=O)NC1CC2CCC1C2)C(O)c1ccccc1Cl]

The substantially same method as described in Example 29 was conducted, except that 2-aminonorbornane was used instead of methylamine solution (CH₃NH₂ in EtOH), to obtain the title compound (1.7 g, yield 20~50%).

¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 36

Synthesis of 1-(2,4-dichlorophenyl)-(S)-1-hydroxypropyl-(S)-2-carbamate (36)

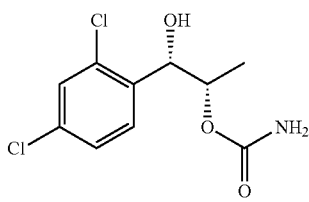 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethylsilanyloxy) propane (Preparation example 69) to obtain the title compound (1.8 g, yield 60~90%).

$^1$H NMR(400 MHz, CDCl$_3$) δ1.22(d, J=6.4 Hz, 3H), 4.16(br t, 1H) 4.96(br t, 3H), 5.07(t, J=4.8 Hz, 1H), 7.23~7.52(m, 3H)

Example 37

Synthesis of 1-(2,6-dichlorophenyl)-(S)-1-hydroxypropyl-(S)-2-carbamate (37)

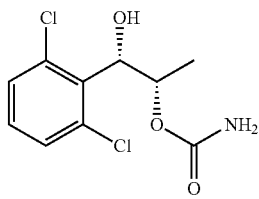 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy) propane (Preparation example 69) to obtain the title compound (2.6 g, yield 60~90%)

Example 38

Synthesis of 1-(2,3-dichlorophenyl)-(S)-1-hydroxypropyl-(S)-2-carbamate (38)

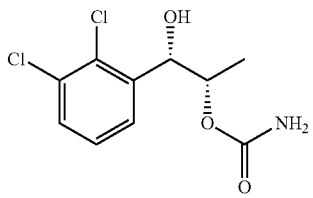 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy) propane (Preparation example 69) to obtain the title compound (1.4 g, yield 60~90%)

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 39

Synthesis of 1-(2,4-dichlorophenyl)-(S)-1-hydroxybutyl-(S)-2-carbamate (39)

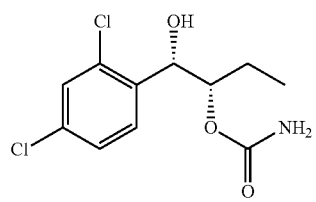

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 40

Synthesis of 1-(2,6-dichlorophenyl)-(S)-1-hydroxybutyl-(S)-2-carbamate (40)

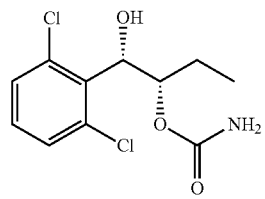

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 41

Synthesis of 1-(2,4-dichlorophenyl)-(S)-1-hydroxy-3-methyl-butyl-(S)-2-carbamate (41)

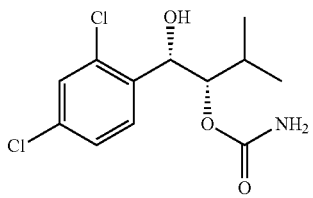 [SMILES: CC(C)[C@H](OC(N)=O)[C@@H](O)c1ccc(Cl)cc1Cl]

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 42

Synthesis of 1-(2,6-dichlorophenyl)-(S)-1-hydroxy-3-methyl-butyl-(S)-2-carbamate (42)

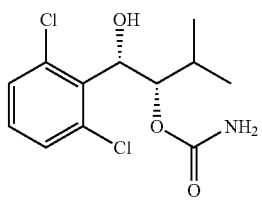 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 43

Synthesis of 1-(2,4-dichlorophenyl)-(S)-1-hydroxy-hexyl-(S)-2-carbamate (43)

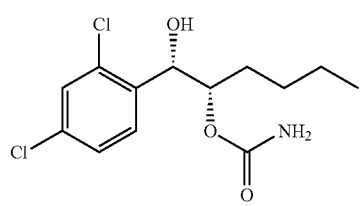 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m 3H)

Example 44

Synthesis of 1-(2,6-dichlorophenyl)-(S)-1-hydroxy-hexyl-(S)-2-carbamate (44)

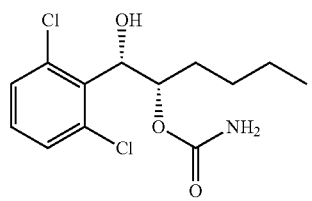 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy) propane (Preparation example 69) to obtain the title compound (2.1 g, yield 60~90%)

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 45

Synthesis of 1-(2,4-dichlorophenyl)-(R)-1-hydroxy-propyl-(R)-2-carbamate (45)

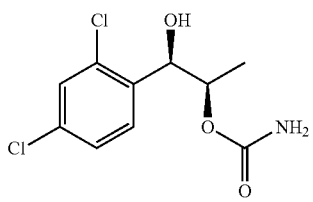 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy) propane (Preparation example 69) to obtain the title compound (1.2 g, yield 60~90%), $^1$H NMR(400 MHz, CDCl$_3$) δ1.22(d, J=6.4 Hz, 3H), 4.16(br t, 1H) 4.96(br t, 3H), 5.07(t, J=4.8 Hz, 1H), 7.23~7.52(m, 3H)

Example 46

Synthesis of 1-(2,6-dichlorophenyl)-(R)-1-hydroxy-propyl-(R)-2-carbamate (46)

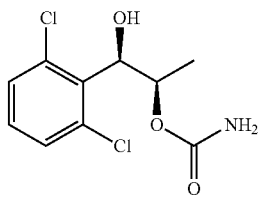 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy) propane (Preparation example 69) to obtain the title compound (1.7 g, yield 60~90%), $^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 47

Synthesis of 1-(2,3-dichlorophenyl)-(R)-1-hydroxy-propyl-(R)-2-carbamate (47)

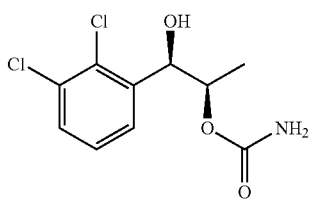 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy) propane (Preparation example 69) to obtain the title compound (2.0 g, yield 60~90%)

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 48

Synthesis of 1-(2,4-dichlorophenyl)-(R)-1-hydroxy-butyl-(R)-2-carbamate (48)

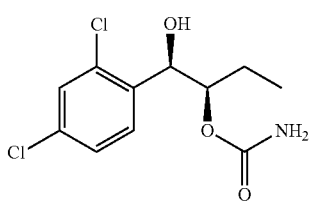 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 49

Synthesis of 1-(2,6-dichlorophenyl)-(R)-1-hydroxy-butyl-(R)-2-carbamate (49)

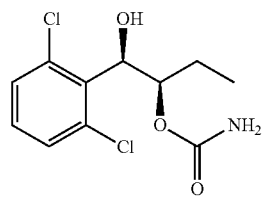 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 50

Synthesis of 1-(2,4-dichlorophenyl)-(R)-1-hydroxy-3-methyl-butyl-(R)-2-carbamate (50)

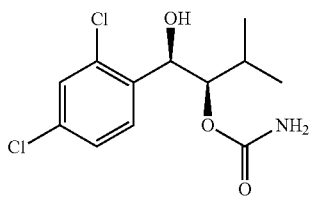 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy) propane (Preparation example 69) to obtain the title compound (2.8 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 51

Synthesis of 1-(2,6-dichlorophenyl)-(R)-1-hydroxy-3-methyl-butyl-(R)-2-carbamate (51)

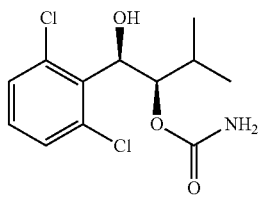 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 52

Synthesis of 1-(2,4-dichlorophenyl)-(R)-1-hydroxy-hexyl-(R)-2-carbamate (52)

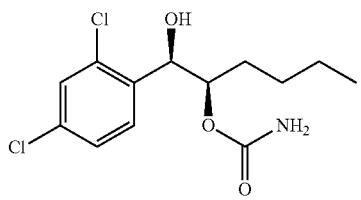 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 53

Synthesis of 1-(2,6-dichlorophenyl)-(R)-1-hydroxy-hexyl-(R)-2-carbamate (53)

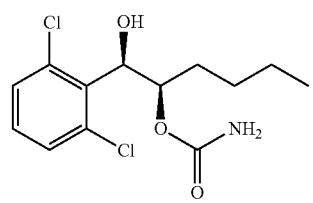 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 54

Synthesis of 1-(2,4-dichlorophenyl)-1-hydroxypropyl-2-carbamate (54)

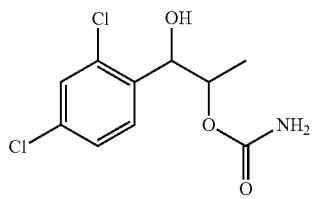 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.22(d, J=6.4 Hz, 3H), 4.16(br t, 1H) 4.96(br t, 3H), 5.07(t, J=4.8 Hz, 1H), 7.23~7.52(m, 3H)

Example 55

Synthesis of 1-(2,6-dichlorophenyl)-1-hydroxypropyl-2-carbamate (55)

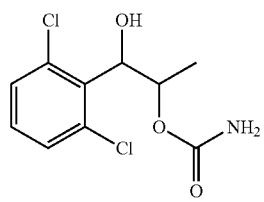 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 56

Synthesis of 1-(2,3-dichlorophenyl)-1-hydroxypropyl-2-carbamate (56)

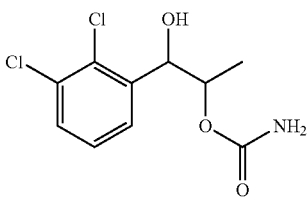 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 57

Synthesis of 1-(2,4-dichlorophenyl)-1-hydroxybutyl-2-carbamate (57)

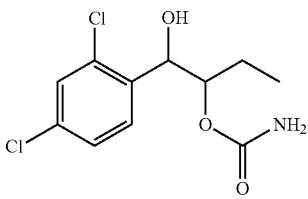 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 58

Synthesis of 1-(2,6-dichlorophenyl)-1-hydroxybutyl-2-carbamate (58)

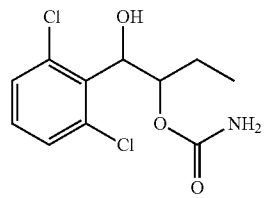 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 59

Synthesis of 1-(2,4-dichlorophenyl)-1-hydroxy-3-methyl-butyl-2-carbamate (59)

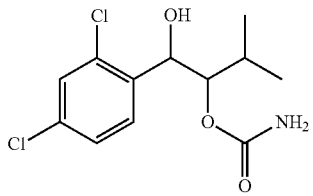

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 60

Synthesis of 1-(2,6-dichlorophenyl)-1-hydroxy-3-methyl-butyl-2-carbamate (60)

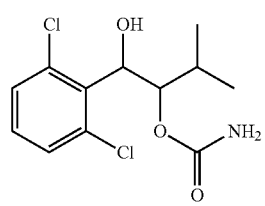 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 61

Synthesis of 1-(2,4-dichlorophenyl)-1-hydroxyhexyl-2-carbamate (61)

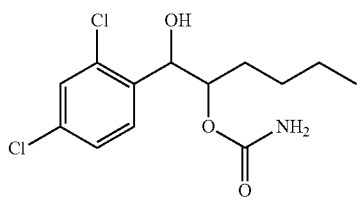 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 62

Synthesis of 1-(2,6-dichlorophenyl)-1-hydroxyhexyl-2-carbamate (62)

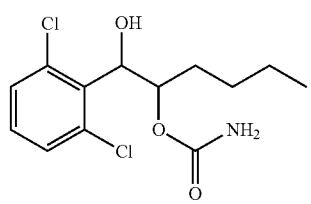 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 63

Synthesis of 1-(2-fluorophenyl)-(S)-1-hydroxypropyl-(S)-2-carbamate (63)

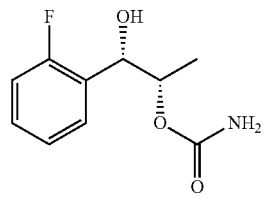

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy) propane (Preparation example 69) to obtain the title compound (1.8 g, yield 60~90%).

$^1$H NMR(400 MHz, CDCl$_3$) δ1.19(d, J=5.2 Hz, 3H), 2.93(d, J=4.4 Hz, 1H), 4.71(br s, 2H), 4.99~5.06(m, H), 7.04~7.48(m, 4H)

Example 64

Synthesis of 1-(2-fluorophenyl)-(R)-1-hydroxypropyl-(R)-2-carbamate (64)

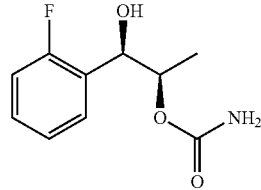

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.19(d, J=5.2 Hz, 3H), 2.93(d, J=4.4 Hz, 1H), 4.71(br s, 2H), 4.99~5.06(m, H), 7.04~7.48(m, 4H)

Example 65

Synthesis of 1-(2-iodophenyl)-(S)-1-hydroxypropyl-(S)-2-carbamate (65)

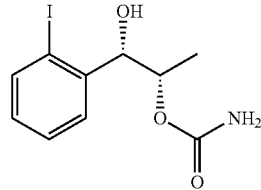

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ1.27(d, J=6.4 Hz, 3H), 3.09(br s, 1H), 4.83(br s, 2H), 5.00~5.10(m, 2H), 7.00~7.76 (m, 4H)

Example 66

Synthesis of 1-(2-iodophenyl)-(R)-1-hydroxypropyl-(R)-2-carbamate (66)

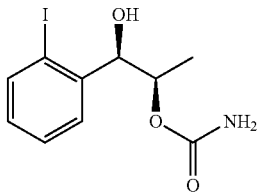

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.27(d, J=6.4 Hz, 3H), 2.95(d, J=3.6 Hz, 1H), 4.73(br s, 2H), 5.01~5.11(m, 2H), 7.01~7.86(m, 4H)

Example 67

Synthesis of 1-(2-iodophenyl)-(S)-1-hydroxybutyl-(S)-2-carbamate (67)

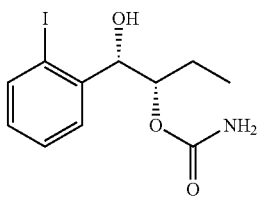 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR(400 MHz, CDCl$_3$) δ1.27(d, J=6.4 Hz, 3H), 3.09(br s, 1H), 4.83(br s, 2H), 5.00~5.10(m, 2H), 7.00~7.76 (m, 4H)

Example 68

Synthesis of 1-(2-chlorophenyl)-(S)-2-hydroxypropyl-(S)-1-carbamate (68)

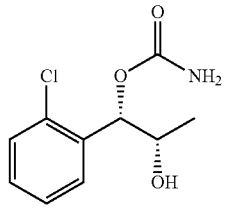

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH$_4$OH, 4 ml) was added thereto. When the reaction was completed, the obtained product was washed with 1M HCl solution and ethylacetate (EA). The separated organic layer was dehydrated with anhydrous magnesium sulfate (MgSO$_4$), filtrated, and concented under reduced pressure. The concentrated residue was purified by a silica gel column chromatography, to obtain the title compound (0.28 g, yield 10~30%).

$^1$H NMR(400 MHz, CDCl$_3$) δ1.24(d, J=6.8 Hz, 3H), 2.13(d, J=4.4 Hz, 1H), 4.12~4.16(m, 1H), 4.85(br s, 2H), 5.98(d, J=5.6 Hz, 1H), 7.24~7.43(m, 4H)

Example 69

Synthesis of 1-(2-chlorophenyl)-(R)-2-hydroxypropyl-(R)-1-carbamate (69)

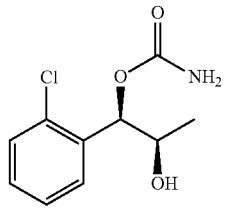

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

$^1$H NMR(400 MHz, CDCl$_3$) δ1.24(d, J=6.4 Hz, 3H), 2.04(d, J=4.8 Hz, 1H), 4.11~4.18(m, 1H), 4.74(br s, 2H), 6.00(d, J=5.6 Hz, 1H), 7.24~7.43(m, 4H)

Example 70

Synthesis of 1-(2-chlorophenyl)-2-hydroxypropyl-1-carbamate (70)

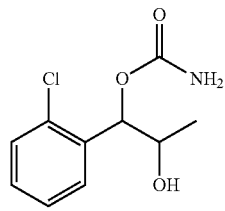

The substantially same method as described in Example 68 was conducted, except that 1-(2-chlorophenyl)-(R,R)-1,2-propanediol (Preparation Example 16) was used instead of 1-(2-chlorophenyl)-(S,S)-1,2-propanediol (Preparation example 14) to obtain the title compound (0.16 g, yield 10~30%).

$^1$H NMR(400 MHz, CDCl$_3$) δ1.24(d, J=6.4 Hz, 3H), 2.04(d, J=4.8 Hz, 1H), 4.11~4.18(m, 1H), 4.74(br s, 2H), 6.00(d, J=5.6 Hz, 1H), 7.24~7.43(m, 4H)

Example 71

Synthesis of 1-(2-chlorophenyl)-(S)-2-hydroxypropyl-(S)-1-N-methylcarbamate (71)

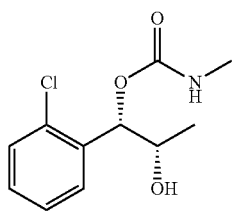 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

$^1$H NMR(400 MHz, CDCl$_3$) δ1.21(d, J=6.4 Hz, 3H), 2.80(d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 72

Synthesis of 1-(2-chlorophenyl)-(R)-2-hydroxypropyl-(R)-1-N-methylcarbamate (72)

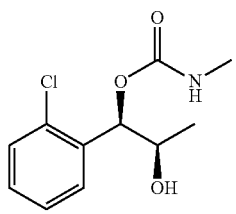 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).

$^1$H NMR(400 MHz, CDCl$_3$) δ1.21(d, J=6.4 Hz, 3H), 2.80(d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 73

Synthesis of 1-(2-chlorophenyl)-2-hydroxypropyl-1-N-methylcarbamate (73)

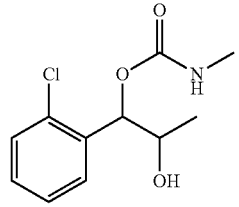 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

$^1$H NMR(400 MHz, CDCl$_3$) δ 1.22(d, J=6 Hz, 3H), 2.15(d, J=4 Hz, 1H), 2.81(d, J=5 Hz, 3H), 4.12(dd, J=6 Hz, 1H), 4.83(br s, 1H), 6.00(d, J=6 Hz, 1H), 7.23~7.41(m, 4H)

Example 74

Synthesis of 1-(2-chlorophenyl)-(S)-2-hydroxypropyl-(S)-1-N-propylcarbamate (74)

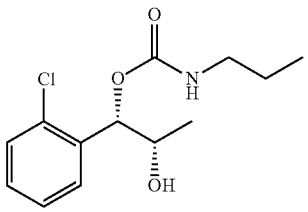 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 75

Synthesis of 1-(2-chlorophenyl)-(R)-2-hydroxypropyl-(R)-1-N-propylcarbamate (75)

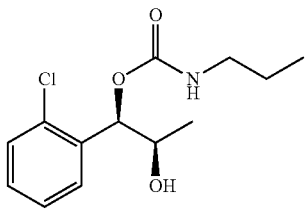 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 76

Synthesis of 1-(2-chlorophenyl)-2-hydroxypropyl-1-N-propylcarbamate (76)

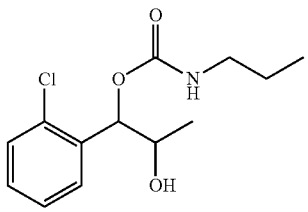 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 77

Synthesis of 1-(2-chlorophenyl)-(S)-2-hydroxypropyl-(S)-1-N-isopropylcarbamate (77)

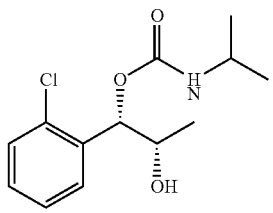 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).

$^1$H NMR(400 MHz, CDCl$_3$) δ 1.10(d, J=6.0 Hz, 3H), 1.15~1.19(m, 6H), 2.41(s, 1H), 3.76~4.08(m, 1H), 4.34(s, 1H), 4.83(br s 1H), 5.95(d, J=5.3 Hz, 1H), 7.19~7.39(m, 4H)

Example 78

Synthesis of 1-(2-chlorophenyl)-(R)-2-hydroxypropyl-(R)-1-N-isopropylcarbamate (78)

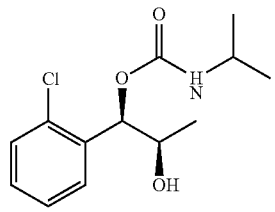 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).

$^1$H NMR(400 MHz, CDCl$_3$) δ1.13(d, J=6 Hz, 3H), 1.20 (dd, J=9.2 Hz, 6H), 2.23(s, 1H), 3.77~3.82(m, 1H), 4.10(s, 1H), 4.76(br s, 1H), 5.98(d, J=5.6 Hz, 1H), 7.23~7.41(m, 4H)

Example 79

Synthesis of 1-(2-chlorophenyl)-2-hydroxypropyl-1-N-isopropylcarbamate (79)

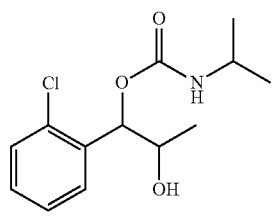 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 10~30%).

$^1$H NMR(400 MHz, CDCl$_3$) δ 1.14(d, J=6 Hz, 3H), 1.21(dd, J=6 Hz, 6H), 2.16(d, J=5 Hz, 1H), 3.81(t, J=6 Hz, 1H), 4.11(d, J=5 Hz, 1H), 4.73(br s, 1H), 5.98(d, J=5 Hz, 1H), 7.24~741(m, 4H)

Example 80

Synthesis of 1-(2-chlorophenyl)-(S)-2-hydroxypropyl-(S)-1-N-cyclopropylcarbamate (80)

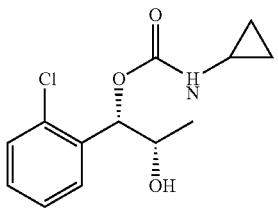 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 81

Synthesis of 1-(2-chlorophenyl)-(R)-2-hydroxypropyl-(R)-1-N-cyclopropylcarbamate (81)

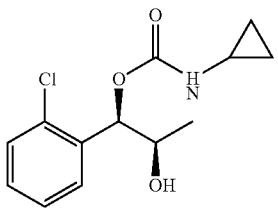 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 82

Synthesis of 1-(2-chlorophenyl)-2-hydroxypropyl-1-N-cyclopropylcarbamate (82)

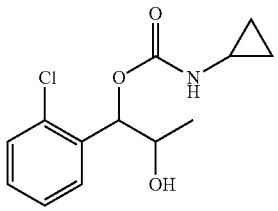 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

$^1$H NMR(400 MHz, CDCl$_3$) δ 0.71(s, 2H), 1.19(d, J=6 Hz, 3H), 2.45(s, 1H), 2.57(s, 1H), 4.08~4.12(m, 1H), 5.26(s, 1H), 5.97(d, J=4 Hz, 1H), 7.22~7.54(m, 4H)

Example 83

Synthesis of 1-(2-chlorophenyl)-(S)-2-hydroxypropyl-(S)-1-N-cyclohexylcarbamate (83)

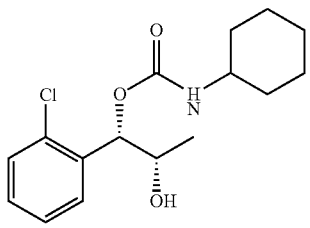 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 84

Synthesis of 1-(2-chlorophenyl)-(R)-2-hydroxypropyl-(R)-1-N-cyclohexylcarbamate (84)

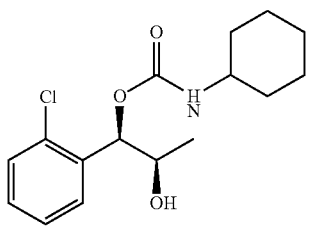 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 85

Synthesis of 1-(2-chlorophenyl)-2-hydroxypropyl-1-N-cyclohexylcarbamate (85)

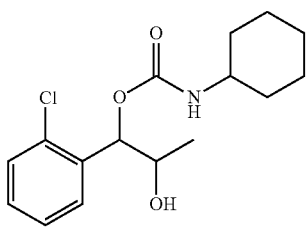 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).

$^1$H NMR(400 MHz, CDCl$_3$) δ1.12~1.19(m, 3H), 1.22(d, J=6 Hz, 3H), 1.27~1.37(m, 1H), 1.71(t, J=6 Hz, 2H), 1.86~1.88(m, 1H), 1.97~2.00(m, 1H), 2.18(d, J=4 Hz, 1H), 3.47(s, 1H), 4.12(t, J=6 Hz, 1H), 4.78(s, 1H), 5.97(d, J=6 Hz, 1H), 7.23~7.40(m, 4H)

Example 86

Synthesis of 1-(2-chlorophenyl)-(S)-2-hydroxypropyl-(S)-1-N-benzylcarbamate (86)

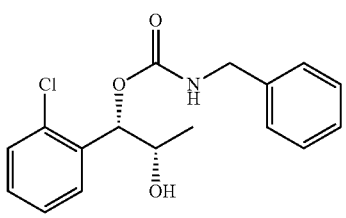 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 87

Synthesis of 1-(2-chlorophenyl)-(R)-2-hydroxypropyl-(R)-1-N-benzylcarbamate (87)

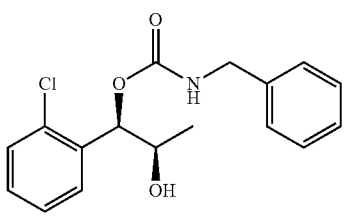 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 88

Synthesis of 1-(2-chlorophenyl)-2-hydroxypropyl-1-N-benzylcarbamate (88)

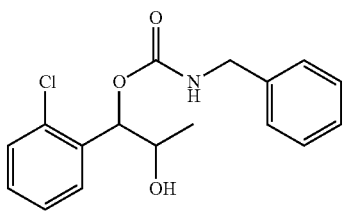 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 89

Synthesis of 1-(2,4-dichlorophenyl)-(S)-2-hydroxypropyl-(S)-1-carbamate (89)

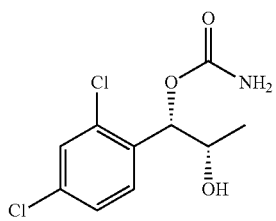 [SMILES: C[C@H](O)[C@@H](OC(N)=O)c1ccc(Cl)cc1Cl]

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30(d, J=8.4 Hz, 1H), 7.39(d, J=2.0 Hz, 2H), 7.50(dd, J=8.4 Hz, 2.0 Hz, 1H)

Example 90

Synthesis of 1-(2,6-dichlorophenyl)-(S)-2-hydroxy-propyl-(S)-1-carbamate (90)

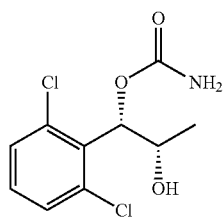 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 91

Synthesis of 1-(2,3-dichlorophenyl)-(S)-2-hydroxy-propyl-(S)-1-carbamate (91)

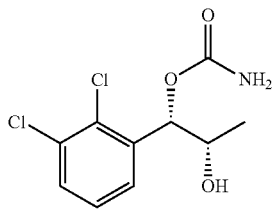 [SMILES: C[C@H](O)[C@@H](OC(N)=O)c1cccc(Cl)c1Cl]

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 92

Synthesis of 1-(2,4-dichlorophenyl)-(S)-2-hydroxy-butyl-(S)-1-carbamate (92)

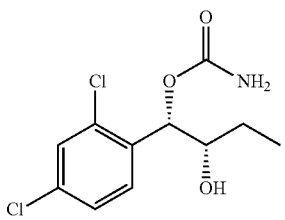 [SMILES: CC[C@H](O)[C@@H](OC(N)=O)c1ccc(Cl)cc1Cl]

The substantially same method as described in Example 68 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 93

Synthesis of 1-(2,6-dichlorophenyl)-(S)-2-hydroxy-butyl-(S)-1-carbamate (93)

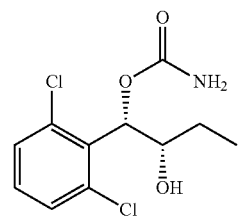 [SMILES: CC[C@H](O)[C@@H](OC(N)=O)c1c(Cl)cccc1Cl]

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 94

Synthesis of 1-(2,4-dichlorophenyl)-(S)-2-hydroxy-3-methyl-butyl-(S)-1-carbamate (94)

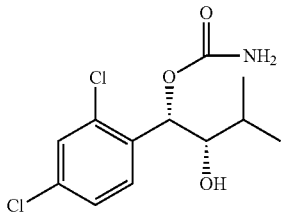 [SMILES: CC(C)[C@H](O)[C@@H](OC(N)=O)c1ccc(Cl)cc1Cl]

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 95

Synthesis of 1-(2,6-dichlorophenyl)-(S)-2-hydroxy-3-methyl-butyl-(S)-1-carbamate (95)

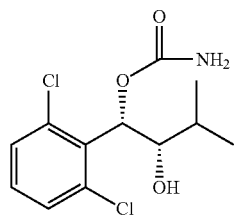 [SMILES: CC(C)[C@H](O)[C@@H](OC(N)=O)c1c(Cl)cccc1Cl]

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 96

Synthesis of 1-(2,4-dichlorophenyl)-(S)-2-hydroxy-hexyl-(S)-1-carbamate (96)

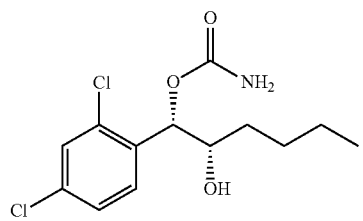 [SMILES: CCCC[C@H](O)[C@@H](OC(N)=O)c1ccc(Cl)cc1Cl]

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 97

Synthesis of 1-(2,6-dichlorophenyl)-(S)-2-hydroxy-hexyl-(S)-1-carbamate (97)

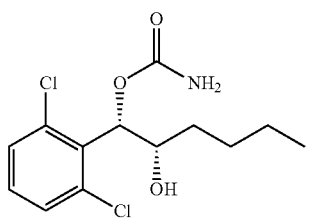 [SMILES: CCCC[C@H](O)[C@@H](OC(N)=O)c1c(Cl)cccc1Cl]

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 98

Synthesis of 1-(2,4-dichlorophenyl)-(R)-2-hydroxy-propyl-(R)-1-carbamate (98)

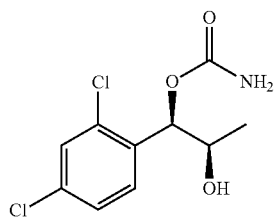 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30~7.50(m, 3H)

Example 99

Synthesis of 1-(2,6-dichlorophenyl)-(R)-2-hydroxy-propyl-(R)-1-carbamate (99)

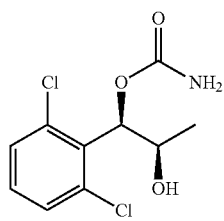 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 100

Synthesis of 1-(2,3-dichlorophenyl)-(R)-2-hydroxy-propyl-(R)-1-carbamate (100)

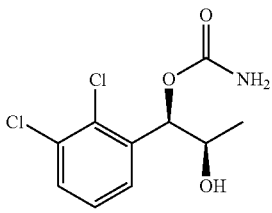 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 101

Synthesis of 1-(2,4-dichlorophenyl)-(R)-2-hydroxy-butyl-(R)-1-carbamate (101)

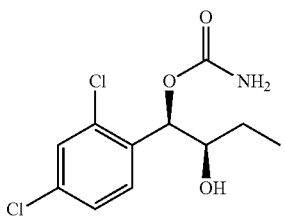 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 102

Synthesis of 1-(2,6-dichlorophenyl)-(R)-2-hydroxy-butyl-(R)-1-carbamate (102)

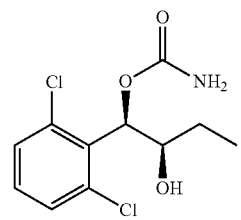 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%). $^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 103

Synthesis of 1-(2,4-dichlorophenyl)-(R)-2-hydroxy-3-methyl-butyl-(R)-1-carbamate (103)

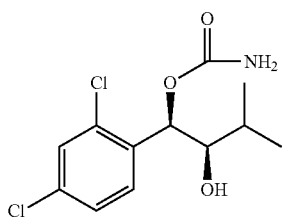 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 104

Synthesis of 1-(2,6-dichlorophenyl)-(R)-2-hydroxy-3-methyl-butyl-(R)-1-carbamate (104)

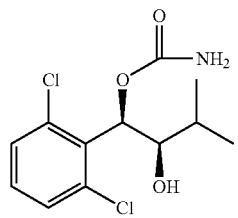 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 105

Synthesis of 1-(2,4-dichlorophenyl)-(R)-2-hydroxy-hexyl-(R)-1-carbamate (105)

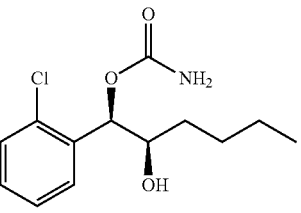

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 106

Synthesis of 1-(2,6-dichlorophenyl)-(R)-2-hydroxy-hexyl-(R)-1-carbamate (106)

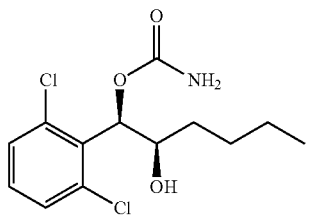 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 107

Synthesis of 1-(2,4-dichlorophenyl)-2-hydroxypropyl-1-carbamate (107)

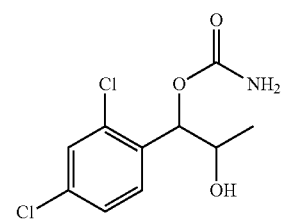 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30~7.50(m, 3H)

Example 108

Synthesis of 1-(2,6-dichlorophenyl)-2-hydroxypropyl-1-carbamate (108)

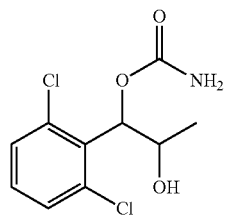 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 109

Synthesis of 1-(2,3-dichlorophenyl)-(R)-2-hydroxypropyl-(R)-1-carbamate (109)

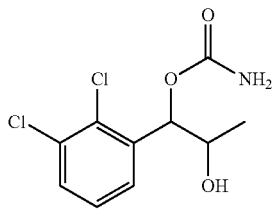 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 110

Synthesis of 1-(2,4-dichlorophenyl)-2-hydroxybutyl-1-carbamate (110)

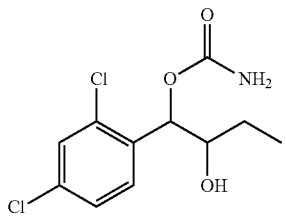

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 111

Synthesis of 1-(2,6-dichlorophenyl)-2-hydroxybutyl-1-carbamate (111)

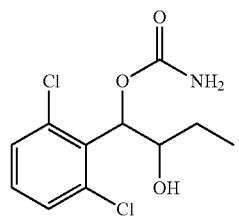 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 112

Synthesis of 1-(2,4-dichlorophenyl)-2-hydroxy-3-methyl-butyl-1-carbamate (112)

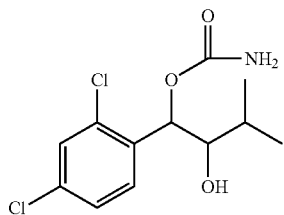

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 113

Synthesis of 1-(2,6-dichlorophenyl)-2-hydroxy-3-methyl-butyl-1-carbamate (113)

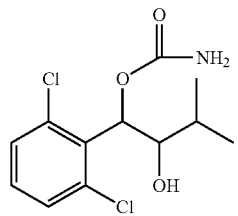 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 114

Synthesis of 1-(2,4-dichlorophenyl)-2-hydroxyhexyl-1-carbamate (114)

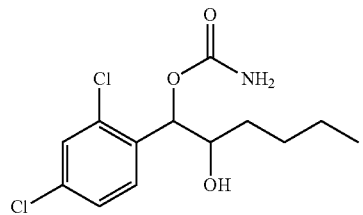 [SMILES: CCCCC(O)C(OC(N)=O)c1ccc(Cl)cc1Cl]

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 115

Synthesis of 1-(2,6-dichlorophenyl)-2-hydroxyhexyl-1-carbamate (115)

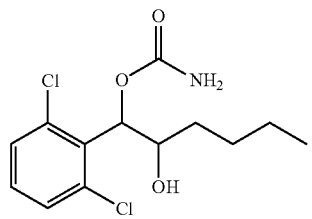 [SMILES: CCCCC(O)C(OC(N)=O)c1c(Cl)cccc1Cl]

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Compounds 1 to 115 produced in Examples 1 to 115 were summarized in following Tables 2 and 3.

TABLE 2

Compounds 1 to 67 having the structure of Chemical Formula 1 where 'A' is a carbamoyl derivative and 'B' is H

| No. | X | n (position) | $1^{st}$ Chiral | $2^{nd}$ Chiral | $R^1$ | A<br>A = carbamoyl derivative<br>$R^2$ = | B<br>B = H |
|---|---|---|---|---|---|---|---|
| 1 | Cl | 1(2-) | S | S | Me | H | H |
| 2 | Cl | 1(2-) | R | R | Me | H | H |

TABLE 2-continued

Compounds 1 to 67 having the structure of Chemical Formula 1 where 'A' is a carbamoyl derivative and 'B' is H

| No. | X | n (position) | $1^{st}$ Chiral | $2^{nd}$ Chiral | $R^1$ | A<br>A = carbamoyl derivative<br>$R^2 =$ | B<br>B = H |
|---|---|---|---|---|---|---|---|
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac. | Rac. | Me | H | H |
| 57 | Cl | 2(2,4-) | Rac. | Rac. | Et | H | H |
| 58 | Cl | 2(2,6-) | Rac, | Rac. | Et | H | H |
| 59 | Cl | 2(2,4-) | Rac, | Rac. | Isopropyl | H | H |
| 60 | Cl | 2(2,6-) | Rac, | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 3

Compounds 68 to 115 having the structure of Chemical Formula 1 where 'A' is H and 'B' is a carbamoyl derivative

| No. | X | n (position) | 1st Chiral | 2nd Chiral | R¹ | A A = H | B B = carbamoyl derivative R³ = |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Example 116

The Chemical Induced Seizure Model

Picrotoxin (PIC) were used to induce the behavioral seizures in the experiments. Male Sprague-Dawley rats or ICR mice (purchased from Orient Bio Inc. Korea) of body weight 100-130 g (rats) or 19-26 g (mice) were used for these studies. The test materials were administered intraperitoneal (ip) route in a volume of 4 ul/g (rats) or 10 ul/g (mice) weight in rats or mice, respectively. Pharmacological effects of the test materials were evaluated to compared test groups (n=6) with a control group (n=6). Control group was administrated vehicle, only. The peak time was determined by administration of test material's random dose for 0.5, 1, 2, 4 hour. The time that the most protect was defined as a peak time and ED50 was determined by other dose administration at the peak time. Chemical (PIC) was dissolved in 0.9% saline and administered subcutaneously (s.c.) at its CD97 (convulsive dose 97%), the dose of Chemical (PIC) that produced clonic seizures in 97% into a loose fold of skin in the midline of the neck in a volume of 2 ul/g (rats) or 10 ul/g (mice) body weight. The animals were then transferred to observation cages and observed continuously for 45 min (PIC). Clonic seizure was elicited in approximately 97% of control group. Protection was defined as a complete absence of clonic seizure over the 30-min or 45-min observation period. The effective dose of compound necessary to protect against generalized convulsive seizures to 50% of controls (i.e. ED50) was determined by log probit analysis using SPSS software program (SPSS Inc.). The obtained results are shown in following Table 1. (Reference; White H. S., J. H. Woodhead, K. S. Wilcox, J. P. Stables, H. J. Kupferberg, and H. H. Wolf. General Principles; Discovery and Preclinical Development of Antiepileptic Drugs. In: R. H. Levy, R.

H. Mattson, B. S. Meldrum, and E. Perucca, eds. Antiepileptic Drugs, 5$^{th}$ Ed. Lippincott Williams & Wilkins, Philadelphia 2002: pp. 36-48.)

TABLE 4

Measurement results of anti-generalized convulsive seizure activity of compounds in the test animals (Mice)

| Compound No. | PIC (ip) ED50 (mg/kg) | Peak Time (h) |
|---|---|---|
| 1 | 18.2 | 2 |
| 2 | 50$^a$ (16.7%) | — |
| 3 | 10$^a$ (50%) | — |
| 4 | 30$^a$ (100%) | — |
| 6 | 50$^a$ (66.7%) | — |
| 8 | 50$^a$ (33.3%) | — |
| 9 | 50$^a$ (16.7%) | — |
| 12 | 50$^a$ (16.7%) | — |
| 13 | 50$^a$ (16.7%) | — |
| 14 | 50$^a$ (16.7%) | — |
| 15 | 50$^a$ (50%) | — |
| 23 | 50$^a$ (16.7%) | — |
| 29 | 50$^a$ (33.3%) | — |
| 30 | 50$^a$ (16.7%) | — |
| 31 | 50$^a$ (16.7%) | — |
| 36 | 50$^a$ (50%) | — |
| 37 | 23.4 | 0.25 |
| 38 | 50$^a$ (50%) | — |
| 39 | 50$^a$ (66.7%) | — |
| 40 | 50$^a$ (66.6%) | — |
| 43 | 50$^a$ (16.6%) | — |
| 44 | 50$^a$ (16.6%) | — |
| 46 | 50$^a$ (33.3%) | — |
| 63 | 60$^a$ (33.3%) | — |
| 65 | 50$^a$ (100%) | — |
| 67 | 50$^a$ (83.3%) | — |

$^a$Injection amount(mg/kg),
% = the percentage of activity compared to the vehicle only, respectively.

Example 117

Multiple-hit rat Model of IS (Infantile Spasms)

This study was used male offspring of timed pregnant Sprague-Dawley rats (Nara biotech, Seoul, Korea). Animal preparation and surgical procedures were as described before (Scantlebury et al., 2010). At postnatal day 3 (PN3), doxorubicin (right intracerebroventricular) and lipopolysaccharide (right intraparietal) were infused stereotactically, under isoflurane anesthesia. At PN4, rats were separated for video monitoring as described (Scantlebury et al., 2010). The monitoring session consisted of 1 hour before injection and 5 hour after injection. The test materials were administered subcutaneously in a volume of 10 ul/g weight. Behavioral spasms were considered the sudden and synchronous high-amplitude movements of all limbs and body to a flexion or extension posture. Flexion or extension events that had asynchronous limb movements or appeared as an attempt of the pup to reposition were excluded to minimize false-positive events (Reference; Scantlebury M. H., Galanopoulou A. G., Chudomelova L., Raffo E., Betancourth D. and Moshe S. L. (2010). A model of symptomatic infantile spasm syndrome. Neurobiol. Dis. 37: 604-612./Ono T., Moshe S. L. and Galanopoulou A. G. (2011). Carisbamate acutely suppresses spasm in a rat model of symptomatic infantile spasms. Epilepsia 52: 1678-1684.) The test result was shown in FIG. 1 and Table 5.

Provided are non-human mammals treated with doxorubicin, lipopolysaccharide (LPS), and p-chlorophenylalanine (PCPA), where the mammal exhibits a symptom characteristic of infantile spasms. Also provided are methods of making a non-human mammal exhibit a symptom of infantile spasms. Additionally, methods are provided for screening a compound for the potential to attenuate a symptom of infantile spasms.

TABLE 5

Measurement results of anti-ACTH(Adrenocorticotropic hormone)-refractory infantile spasm activity of compounds in the test animals (Rats)

| Compound (Example) No. | ACTH-refractory IS (ip) ED50 (mg/kg) | Peak Time (h) |
|---|---|---|
| 1 | 19.8 | 1 |
| 2 | 60$^a$ (65.9%) | 1 |
| 3 | 60$^a$ (34%) | 3 |
| 4 | 60$^a$ (24.3%) | 3 |
| 6 | 60$^a$ (76.2%) | 3 |
| 15 | 60$^a$ (67.44%) | 2 |
| 36 | 60$^a$ (37.5%) | 3 |
| 37 | 60$^a$ (83.8%) | 3 |
| 46 | 60$^a$ (78%) | 3 |
| 47 | 60$^a$ (91%) | 3 |
| 65 | 60$^a$ (92.1%) | 3 |
| 67 | 60$^a$ (81.1%) | 2 |

$^a$Injection amount (mg/kg),
Protection % (6 mice), % = the percentage of activity compared to the vehicle only, respectively.

Example 118

Minimal Clonic Seizure (6 Hz) Test

Some clinically useful AEDs are ineffective in the standard MES and scPTZ tests but still have anticonvulsant activities in vivo. In order to identify potential AEDs with this profile, compounds may be tested in the minimal clonic seizure (6 Hz or 'psychomotor') test (Barton et al., 2001). Like the maximal electroshock (EMS) test, the minimal clonic seizure (6 Hz) test is used to assess a compound's efficacy against electrically induced seizures but used a lower frequency (6 Hz) and longer duration of stimulation (3 s).

Test compound is pre-administrated to mice via i.p. injection. At varying times, individual mice (four per time point) are challenged with sufficient current delivered through corneal electrodes to elicit a psychomotor seizure in 97% of animals (32 mA or 44 mA for 3 s) (Toman et al., 1952). Untreated mice will display seizures characterized by a minimal clonic phase followed by stereotyped, automatistic behaviors described originally as being similar to the aura of human patients with partial seizures. Animals not displaying this behavior are considered protected. The test may be evaluated quantitatively by measuring the response at varying doses at a determined time of peak effect (TPE).

The obtained results are shown in following Table 6 (Reference; Barton M. E., Klein B. D., Wolf H. H. and White H. S. (2001). Pharmacological characterization of the 6 Hz psychomotor seizure model of partial epilepsy. Epilepsy Res. 47: 217-227./Toman J. E., Everett G. M. and Richards R. K. (1952). The search for new drugs against epilepsy. Tex. Rep. Biol. Med. 10: 96-104.)

TABLE 6

Measurement results of 6 Hz-induced seizure of 1-(2-chlorophenyl)-(S)-1-hydroxypropyl-(S)-2-carbamate (Compound 1) in the test(Mice)

| | 6 Hz | | |
|---|---|---|---|
| Assay | 32 mA | 44 mA | Peak Time (h) |
| ED50 (mg/kg) | 14.6 | 13.66 | 0.25 |

Example 116

Lithium-pilocarpine Induced Status Epilepticus Model

Prevention Study

Male Sprague-Dawley rats (purchased from Orient Bio Inc. Korea) of body weight 200-230 g were used for these studies and housed 4-5 rats per a cage for 4-5 days. On the day prior to status epilepsy (SE), rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The test drug was administered intraperitoneally (i.p.) in a volume of 2 ul/g body weight. Pharmacological effects of all the test materials were evaluated to compare the test groups (n=6) with a control group (n=6). Control group was administrated vehicle, only. The peak time was determined by administration test material's random dose for 0.5, 1, 2, 4 hour. The time that the most protect was defined peak time and ED50 was determined by other dose administration at peak time. The animals were then transferred to observation cages and observed continuously for 90 min. The seizure activity was elicited in approximately 95% of control group. Protection was defined as a complete absence of seizure grade 4~5 based on Racine scale (Racine, 1972) over the 90-min observation period. The effective dose of compound necessary to protect against seizures to 50% of controls (i.e. ED50) was determined by log probit analysis using SPSS software program (SPSS Inc.). The obtained results are shown in following Table 6.

Intervention Study

Male Sprague-Dawley rats (purchased from Orient Bio Inc. Korea) of body weight 200-230 g were used for these studies and housed 4-5 rats per a cage for 4-5 days. On the day prior to SE, rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The effects of compounds dissolved in 30% Poly Ethylene Glycol 400 (Acros Organics, Geel, Belgium) 20% Tween80 were studied at various times or 30 min after the occurrence of the first motor seizure or SE onset. The drug was administered intraperitoneally in a volume of 2 ul/g body weight. Pharmacological effects was evaluated to compare the test groups with a control group (n=8). Control group was administrated vehicle, only. The obtained results are shown in following Table 8 (Reference; Racine R. J. (1972). Modification of seizure activity by electrical stimulation: II Motor seizure. Electroenceph. Clin. Neurophysiol. 32: 281-294.)

TABLE 7

Measurement results of Lithium-pilocarpine induced status epilepticus of compounds in the prevention test (Rats)

| | Therapeutic effect Prevention (rat, ip) | |
|---|---|---|
| Compound (Example) No. | ED50 (mg/kg) | Peak Time (h) |
| 1 | 18.0 | 2 |
| 2 | 71.9 | 0.5 |
| 3 | 31.7 | 0.5 |
| 4 | $^a$60 (50%) | — |
| 6 | $^a$60 (100%) | — |
| 8 | $^a$60 (83.3%) | — |
| 9 | $^a$60 (83.3%) | — |
| 25 | $^a$60 (100%) | — |
| 29 | $^a$60 (100%) | — |
| 30 | $^a$73.6 (50%) | — |
| 32 | $^a$60 (100%) | — |
| 36 | $^a$73.6 (100%) | — |
| 37 | $^a$35 (100%) | — |
| 38 | $^a$73.6 (100%) | — |
| 42 | $^a$60 (83.3%) | — |
| 46 | $^a$60 (66.7%) | — |
| 63 | 49.3 | 0.25 |
| 65 | 15.3 | 2 |
| 67 | 28.2 | 0.5 |

$^a$Injection amount (mg/kg),
Protection % = the percentage of prevention activity compared to the vehicle only, respectively.

TABLE 8

Measurement results of Lithium-pilocarpine induced status epilepticus of compounds in the intervention test (Rats)

| Compound (Example) No. | Intervention (rat, iv) ED50 (mg/kg) |
|---|---|
| 1 | 22.6 |
| 2 | $^a$46 (50%) |
| 3 | $^a$46 (83.3%) |
| 4 | $^a$46 (100%) |
| 5 | $^a$46 (66.7%) |
| 6 | $^a$46 (100%) |
| 8 | $^a$46 (50%) |
| 9 | $^a$46 (66.7%) |
| 15 | $^a$46 (100%) |
| 16 | $^a$46 (100%) |
| 18 | $^a$46 (66.7%) |
| 23 | $^a$46 (100%) |
| 25 | $^a$46 (100%) |
| 30 | $^a$46 (83.3%) |
| 31 | $^a$46 (100%) |
| 32 | $^a$46 (100%) |
| 36 | $^a$46 (66.7%) |
| 37 | $^a$46 (100%) |
| 38 | $^a$46 (50%) |
| 40 | $^a$46 (100%) |
| 42 | $^a$46 (66.7%) |
| 43 | $^a$46 (16.7%) |
| 44 | $^a$46 (83.3%) |
| 45 | $^a$46 (33.3%) |
| 46 | $^a$46 (50%) |
| 63 | $^a$46 (50%) |
| 65 | $^a$46 (100%) |
| 67 | $^a$46 (100%) |

$^a$Injection amount (mg/kg),
Protection % = the percentage of prevention activity compared to the vehicle only, respectively.

PTZ (Pentylenetetrazol) Test
The obtained results are shown in following Tables 8 and 9. In this experiment, administered intraperitoneally or orally to test animals (Mouse; ICR, and Rats; SD); Experimental animal, male SD rats, were purchased from Orient-Bio or Nara biotech, Korea, and housed 4-5 mice per a cage for 4-5 days. The range of mice body weight was used between 19 and 26 grams and range of rats body weight was used between 100 and 130 grams. After Peak time (0.5, 1, 2 and 4 hr) from the administration, PTZ (Pentylenetetrazol) was administered subcutaneously in the concentration capable of inducing 97% intermittent convulsions (mice & rats: 90~110 mg/kg·bw, 2 µl/g). If clonic seizure was not observed for at least 3 seconds in the PTZ administered animal, it can be considered that the test compound has anti-nonconvulsive seizure activity. The median effective dose (ED50) is determined using 6 animals per a concentration (total three different concentrations), and calculated by Litchfield and Wicoxon log-probit method which is a dose-response relationship. The obtained results are shown in following Tables 9 and 10.

TABLE 9

Measurement results of anti-nonconvulsive seizure activity of compounds in the test animals (Mice)

| Compound No. | PTZ test (ip) in Mice | |
|---|---|---|
| | ED50 (mg/kg) | Peak Time (h) |
| 1 | 15.8 | 2 |
| 2 | 38.8 | 0.5 |
| 3 | 15.3 | 0.5 |
| 4 | 26.7 | 0.5 |
| 5 | 15.0 | 0.5 |
| 6 | 17.9 | 0.5 |
| 8 | [a]20.4 (50%) | — |
| 9 | [a]20.4 (33.3%) | — |
| 12 | [a]20.4 (33.3%) | — |
| 13 | [a]20.4 (50%) | — |
| 14 | [a]20.4 (16.7%) | — |
| 23 | [a]20.4 (50%) | — |
| 25 | [a]20.4 (66.7%) | — |
| 29 | [a]20.4 (33.3%) | — |
| 30 | [a]20.4 (33.3%) | — |
| 31 | [a]20.4 (83.3%) | — |
| 32 | [a]20.4 (16.7%) | — |
| 36 | [a]20.4 (33.3%) | — |
| 37 | 25.7 | 0.25 |
| 38 | [a]20.4 (50%) | — |
| 39 | 24.3 | 0.5 |
| 40 | [a]20.4 (33.3%) | — |
| 42 | [a]20.4 (50%) | — |
| 44 | [a]20.4 (33.3%) | — |
| 45 | [a]20.4 (16.7%) | — |
| 46 | [a]20.4 (50%) | — |
| 63 | [a]20.4 (50%) | — |
| 65 | [a]20.4 (100%) | — |
| 67 | 23.1 | 0.5 |

[a]Injection amount (mg/kg), Protection % (Mice)
*: Peak Time (h)

TABLE 10

Measurement results of anti-nonconvulsive seizure activity of compounds in the test animals(Rats)

| Compound No. | PTZ test (ip) in Rats ED50 (mg/kg) |
|---|---|
| 2 | 51.9 (*1) |
| 3 | 18.9 (*0.5) |
| 4 | [b]30 (50%) |
| 6 | [b]30 (50%) |
| 15 | [b]25 (33.3%) |
| 16 | [b]30 (33.3%) |
| 18 | [b]30 (16.7%) |

TABLE 10-continued

Measurement results of anti-nonconvulsive seizure activity of compounds in the test animals(Rats)

| Compound No. | PTZ test (ip) in Rats ED50 (mg/kg) |
|---|---|
| 37 | [b]30 (50%) |
| 43 | [b]25 (33.3%) |
| 45 | [b]50 (16.7%) |
| 67 | [b]30 (33.3%) |

[b]Injection amount (mg/kg), Protection % (Rats),
*: Peak Time (h)

What is claimed is:

1. A method of treating pediatric epilepsy or pediatric epilepsy-related syndrome in a pediatric subject, comprising administering a therapeutically effective amount of a compound of chemical formula 1 or a pharmaceutically acceptable salt thereof to a pediatric subject in need of treatment:

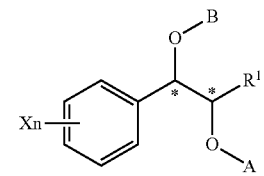

(chemical formula 1),
wherein,
X is a halogen,
n is an integer from 1 to 5,
$R^1$ is a linear or branched alkyl group of $C_1$-$C_4$,
A is a carbamoyl group represented by

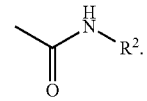

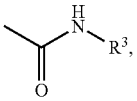

and
$R^2$ is selected from the group consisting of hydrogen, a linear or branched alkyl group of $C_1$-$C_4$, a cycloalkyl group of $C_3$-$C_8$, and benzyl group, and
with the proviso that:
$R^1$ is methyl, propyl or butyl when at least one X is 2-chloro.

2. The method according to claim 1, wherein the phenyl carbamate compound is in the form of racemate, enantiomer, diastereomer, a mixture of enantiomer, or a mixture of diastereomer.

3. The method according to claim 1, wherein X is chlorine, fluorine, iodine, or bromine; n is 1 or 2; and $R^2$ and $R^3$ are the same as or different from each other, and independently selected from the group consisting of hydrogen, methyl group, propyl group, isopropyl group, cyclopropyl group, cyclohexyl group, bicycloheptane group, and benzyl group.

4. The method according to claim 1, wherein the phenyl carbamate compound is selected from the group consisting of:

1-(2-chlorophenyl)-1-hydroxypropyl-2-carbamate, 1-(2-chlorophenyl)-1-hydroxy-3-methyl-butyl-2-carbamate, 1-(2-chlorophenyl)-1-hydroxyhexyl-2-carbamate, 1(2-chlorophenyl)-1-hydroxypropyl-2-N-methylcarbamate, 1(2-chlorophenyl)-1-hydroxypropyl-2-N-propylcarbamate, 1-(2-chlorophenyl)-1-hydroxypropyl-2-N-isopropylcarbamate, 1-(2-chlorophenyl)-1-hydroxypropyl-2-N-cyclopropylcarbamate, 1-(2-chlorophenyl)-1-hydroxypropyl-2-N-cyclohexylcarbamate, 1-(2-chlorophenyl)-1-hydroxypropyl-2-N-benzylcarbamate, 1-(2-chlorophenyl)-1-hydroxypropyl-2-N-bicyclo[2,2,1]heptanecarbamate, 1-(2,4-dichlorophenyl)-1-hydroxypropyl-2-carbamate, 1-(2,6-dichlorophenyl)-1-hydroxypropyl-2-carbamate, 1-(2,4-dichlorophenyl)-1-hydroxybutyl-2-carbamate, 1-(2,4-dichlorophenyl)-1-hydroxy-3-methyl-butyl-2-carbamate, 1-(2,6-dichlorophenyl)-1-hydroxy-3-methyl-butyl-2-carbamate, 1-(2,4-dichlorophenyl)-1-hydroxyhexyl-2-carbamate, 1-(2,6-dichlorophenyl)-1-hydroxyhexyl-2-carbamate, 1-(2-fluorophenyl)-1-hydroxypropyl-2-carbamate, 1-(2-iodophenyl)-1-hydroxypropyl-2-carbamate and 1-(2-iodophenyl)-1-hydroxybutyl-2-carbamate, 1-(2,3-dichlorophenyl)-1-hydroxypropyl-2-carbamate.

5. The method according to claim 1, herein the phenyl carbamate compound is selected from the group consisting of:

1-(2-chlorophenyl)-(S)-1-hydroxypropyl-(S)-2-carbamate, 1-(2-chlorophenyl)-(R)-1-hydroxypropyl-(R)-2-carbamate, racemate of 1-(2-chlorophenyl)-(S)-1-hydroxypropyl-(S)-2-carbamate and 1-(2-chlorophenyl)-(R)-1-hydroxypropyl-(R)-2-carbamate, 1-(2-chlorophenyl)-(R)-1-hydroxypropyl-(S)-2-carbamate, 1-(2-chlorophenyl)-(S)-1-hydroxypropyl-(R)-2-carbamate, 1-(2-chlorophenyl)-(S)-1-hydroxybutyl-(S)-2-carbamate, racemate of 1-(2-chlorophenyl)-(S)-1-hydroxybutyl-(S)-2-carbamate and 1-(2-chlorophenyl)-(R)-1-hydroxybutyl-(R)-2-carbamate, 1-(2-chlorophenyl)-(S)-1-hydroxy-3-methyl-butyl-(S)-2-carbamate, racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate, 1-(2-chlorophenyl)-(S)-1-hydroxypropyl-(S)-2-N-methylcarbamate, 1-(2-chlorophenyl)-(S)-1-hydroxypropyl-(S)-2-N-propylcarbamate, 1-(2-chlorophenyl)-(S)-1-hydroxypropyl-(R)-2-N-isopropylcarbamate, 1-(2-chlorophenyl)-(S)-1-hydroxypropyl-(R)-2-N-cyclopropylcarbamate, 1-(2-chlorophenyl)-(S)-1-hydroxypropyl-(R)-2-N-cyclohexyl carbamate, 1-(2-chlorophenyl)-(R)-1-hydroxypropyl-(R)-2-N-methylcarbamate, 1-(2-chlorophenyl)-(R)-1-hydroxypropyl-(R)-2-N-propylcarbamate, 1-(2-chlorophenyl)-(R)- 1-hydroxypropyl-(R)-2-N-isopropylcarbamate, 1-(2-chlorophenyl)-(R)-1-hydroxypropyl-(R)-2-N-cyclopropylcarbamate,1-(2-chlorophenyl)-(R)-1-hydroxypropyl-(R)-2-N-cyclohexyl carbamate, racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate, racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate, racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate, racemate of 1-(2-chlorophenyI)-(S)-1-hydroxypropyl-(S)-2-N-cyclohexylcarbamate and 1-(2-chlorophenyl)-(R)-1-hydroxypropyl-(R)-2-N-cyclohexylcarbamate, 1-(2-fluorophenyl)-(S)-1-hydroxypropyl-(S)-2-carbamate, 1-(2-fluorophenyl)-(R)-1-hydroxypropyl-(R)-2-carbamate, 1-(2-iodophenyl)-(S)-1-hydroxypropyl-(S)-2-carbamate, 1-(2-iodopheny)-(R)-1-hydroxypropyl-(R)-2-carbamate, and 1-(2-iodophenyl)-(S)-1-hydroxybutyl-(S)-2-carbamate.

6. The method according to claim 1, wherein the pediatric epilepsy or a pediatric epilepsy-related syndrome is selected from the group consisting of Benign Myoclonic Epilepsy (BME), Severe Myoclonic Epilepsy of Infancy Borderland (SMEB), Severe Infantile Multifocal Epilepsy(SIMFE), and Intractable Childhood Epilepsy with Generalized Tonic Clonic Seizures(ICE-GTC), Dravet syndrome(Ds), Severe Myoclonic Epilepsy of Infancy (SMEI), Benign neonatal convulsions, Benign neonatal familial convulsions, Miscellaneous neonatal seizures, Febrile seizures, Early infantile epileptic encephalopathy, Early myoclonic encephalopathy, Infantile spasm, West syndromes Severe myoclonic epilepsy of infancy, Benign myoclonic epilepsy of infancy, Benign partial epilepsy of infancy, Benign infantile familial convulsion, Symptomatic/cryptogenic partial epilepsies, Epilepsy with myoclonic absences, Lennox-Gastaut syndrome, Epilepsy with myoclonic-astatic seizures (Doose syndrome), Acquired epileptic aphasia (Landaw-Kleffner syndrome), Epilepsy with continuous spike-wave during low-wave sleep, Epilepsy with gastric seizures and hypothalamic hamartoma, Symptomatic / cryptogenic partial epilepsies, and Childhood absence epilepsy.

* * * * *

UNITED STATES PATENT AND TRADEMARK OFFICE
CERTIFICATE OF CORRECTION

PATENT NO. : 9,956,197 B2
APPLICATION NO. : 15/190123
DATED : May 1, 2018
INVENTOR(S) : Yong Moon Choi Page 1 of 2

It is certified that error appears in the above-identified patent and that said Letters Patent is hereby corrected as shown below:

On the Title Page

In item (*), in "Notice", in Column 1, Line 3, delete "days. days." and insert --days.-- therefor In the Claims In Column 118, Line 19, in Claim 1, after "thereof", insert --,--

In Column 118, Lines 45-49, in Claim 1, delete " 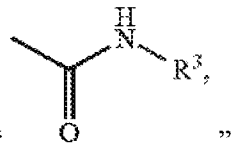 "

In Column 118, Line 50, in Claim 1, before "and", insert --B is hydrogen,--

In Column 119, Lines 6-9, in Claim 4, delete "1(2-chlorophenyl)-1-hydroxypropyl-2-N-methylcarbamate, 1(2-chlorophenyl)-1-hydroxypropyl-2-N-propylcarbamate," and insert --1-(2-chlorophenyl)-1-hydroxypropyl-2-N-methylcarbamate, 1-(2-chlorophenyl)-1-hydroxypropyl-2-N-propylcarbamate,-- therefor In Column 119, Line 26, in Claim 4, delete "carbamate and" and insert --carbamate,-- therefor In Column 119, Line 27, in Claim 4, delete "carbamate," and insert --carbamate and-- therefor In Column 119, Line 29, in Claim 5, delete "herein" and insert --wherein-- therefor In Column 120, Line 6, in Claim 5, delete "cyclopropylcarbamate,1-(2-" and insert --cyclopropylcarbamate, 1-(2- -- therefor Signed and Sealed this
Ninth Day of April, 2019

Andrei Iancu
*Director of the United States Patent and Trademark Office*

In Column 120, Line 20, in Claim 5, delete "1-(2-chlorophenyl)-" and insert --1-(2-chlorophenyl)- -- therefor In Column 120, Lines 26-27, in Claim 5, delete "1-(2-iodopheny)-(R)-1-hydroxypropyl-(R)-2-carbamate," and insert --1-(2-iodophenyl)-(R)-1-hydroxypropyl-(R)-2-carbamate,-- therefor